(12) United States Patent
Yoshida et al.

(10) Patent No.: US 9,439,865 B2
(45) Date of Patent: Sep. 13, 2016

(54) COATING FILM, AND GRANULES AND TABLETS EACH UTILIZING SAME

(71) Applicant: ASAHI KASEI CHEMICALS CORPORATION, Tokyo (JP)

(72) Inventors: Naoya Yoshida, Tokyo (JP); Kazuhiro Obae, Tokyo (JP)

(73) Assignee: ASAHI KASEI CHEMICALS CORPORATION, Tokyo (JP)

( * ) Notice: Subject to any disclaimer, the term of this patent is extended or adjusted under 35 U.S.C. 154(b) by 0 days.

(21) Appl. No.: 14/561,987

(22) Filed: Dec. 5, 2014

(65) Prior Publication Data

US 2015/0104513 A1 Apr. 16, 2015

Related U.S. Application Data

(63) Continuation of application No. 13/499,326, filed as application No. PCT/JP2010/067537 on Oct. 6, 2010, now Pat. No. 8,992,988.

(30) Foreign Application Priority Data

Oct. 9, 2009 (JP) ................. 2009-235284

(51) Int. Cl.
| | | |
|---|---|---|
| *A61K 47/38* | (2006.01) | |
| *A61K 9/20* | (2006.01) | |
| *A61K 47/02* | (2006.01) | |
| *A61K 47/32* | (2006.01) | |
| *C09D 101/00* | (2006.01) | |
| *C09D 101/08* | (2006.01) | |
| *C09D 133/08* | (2006.01) | |
| *C09D 133/10* | (2006.01) | |
| *C09D 129/04* | (2006.01) | |
| *A61K 9/50* | (2006.01) | |
| *A61K 9/16* | (2006.01) | |
| *A61K 31/522* | (2006.01) | |

(52) U.S. Cl.
CPC ........... *A61K 9/2054* (2013.01); *A61K 9/1611* (2013.01); *A61K 9/1617* (2013.01); *A61K 9/1635* (2013.01); *A61K 9/1652* (2013.01); *A61K 9/2009* (2013.01); *A61K 9/2013* (2013.01); *A61K 9/2027* (2013.01); *A61K 9/5026* (2013.01); *A61K 31/522* (2013.01); *C09D 101/08* (2013.01); *C09D 129/04* (2013.01); *C09D 133/08* (2013.01); *C09D 133/10* (2013.01)

(58) Field of Classification Search
CPC C09D 133/09; C09D 133/10; C09D 129/04; C09D 101/08; A61K 31/522; A61K 9/1611; A61K 9/1617; A61K 9/1635; A61K 9/1652; A61K 9/2009; A61K 9/2013; A61K 9/2027; A61K 9/2054; A61K 9/5026
See application file for complete search history.

(56) References Cited

U.S. PATENT DOCUMENTS

| 8,268,356 B2 | 9/2012 | Yoshida et al. |
| 8,765,187 B2 * | 7/2014 | Yaginuma ............ A61K 9/2081 424/464 |
| 2004/0228802 A1 | 11/2004 | Chang et al. |
| 2005/0287211 A1 | 12/2005 | Yoshida et al. |
| 2009/0142378 A1 | 6/2009 | Frisbee |
| 2010/0172978 A1 | 7/2010 | Yaginuma et al. |
| 2010/0209504 A1 | 8/2010 | Yaginuma et al. |
| 2010/0260839 A1 | 10/2010 | Yoshida et al. |

FOREIGN PATENT DOCUMENTS

| EP | 0347024 A2 | 12/1989 |
| EP | 0409254 A1 | 1/1991 |
| JP | 8-109126 | 4/1996 |
| JP | 2000-128776 | 5/2000 |
| JP | 2007-15966 | 1/2007 |
| WO | 88/03795 A1 | 6/1988 |
| WO | 2009/011367 | 1/2009 |
| WO | 2009/028487 A1 | 3/2009 |
| WO | 02/02083 | 1/2012 |

OTHER PUBLICATIONS

Search report from International Application No. PCT/JP2010/067537, mail date is Dec. 7, 2010.
Takao Mizumoto et al., "Formulation Design of Taste-Masked Particles, Including Famotidine, for an Oral Fast-Disintegrating Dosage Form", Chem. Pharm. Bull. 56(4), pp. 530-535, 2008.
European Search Report issued with respect to application No. 10822040.1, mail date is Mar. 16, 2016.
European Search Report issued with respect to application No. 10822040.1, mail date is Dec. 8, 2014.
Shin-ichiro Kimura et al., "Effect of granule properties on rough mouth feel and palatability of orally disintegrating tablets", International Journal of Pharmaceutics, 484 (2015), pp. 156-162.

* cited by examiner

*Primary Examiner* — Abigail Fisher
(74) *Attorney, Agent, or Firm* — Greenblum & Bernstein, P.L.C.

(57) ABSTRACT

A coating film comprising ethyl cellulose as a component A and an (ethyl acrylate)-(methyl methacrylate) copolymer or a plasticized vinyl acetate polymer as a component B, and having a tensile elongation of 150% or more and a tensile strength of 9 N or more.

9 Claims, 16 Drawing Sheets

COATING FILM, AND GRANULES AND TABLETS EACH UTILIZING SAME

The present application is a continuation of U.S. application Ser. No. 13/499,326, which is a National stage of International Patent Application No. PCT/JP2010/067537 filed Oct. 6, 2010, which claims priority to Japanese Application No. 2009-235284 filed Oct. 9, 2009. The disclosures of U.S. application Ser. No. 13/499,326 and International Patent Application No. PCT/JP2010/067537 are incorporated by reference herein in their entireties.

TECHNICAL FIELD

The present invention relates to a coating film, a granule produced using the same and further a tablet containing such a granule, and relates to a quick-disintegrating tablet in the buccal cavity which can be taken without water, is free of the bitter taste of a drug in the buccal cavity, has quick-disintegrating properties, quick dissolution properties as well as a suitable hardness.

BACKGROUND ART

Pharmaceutical solid preparations are sometimes film coated for the purpose of reducing side effects, decreasing the administration frequency, masking the bitter taste of a drug, etc. The film coating is applicable to a tablet and a granular agent but is often applied to granular agents to reduce the unevenness of the coating film. In particular, since the drug dissolution rate must be precisely controlled, spherical core particles having a uniform particle size are commonly used. Further, the most preferred dosage form in the pharmaceutical solid preparations by patients is a tablet, thus it is desired that other excipients be added to the film-coated granule to form a tablet. Furthermore, to enhance the patient compliance, a preparation formulated into a quick-disintegrating tablet in the buccal cavity which can be taken without water is even more desirable.

The common technology for producing a tablet is the compression molding using a tableting machine. In order to assure the practical productivity, handleability and transportability of tablets, the tablet hardness must be increased by compression-molding with a certain level of pressure. However, this pressure often damages the film of the film-coated granules, causing the loss of the drug dissolution functions and the loss of masking effect on the bitter taste of a drug. Thus, the coating with a plurality of films, and the like, have been attempted.

It is very advantageous in terms of productivity to complete a film coating step using one kind of film. A method that allows a film to withstand mechanical stress during tableting is to impart the film with the flexibility like rubber. However, a highly flexible film also has a highly tacky film surface, likely causing granules to agglomerate during the film coating. To prevent the granule agglomeration during the film coating, there are counteractive techniques such as using large granules, reducing the coating rate of a film coating liquid, and adding a tackiness-reducing agent such as talc to a film coating liquid. However, it is conventionally difficult to cope with various sizes of granules without sacrificing the productivity and film properties (drug dissolution control, masking control of the bitter taste of a drug and mechanical strengths).

It is known that a film made from an ethyl acrylate/methyl methacrylate copolymer and a vinyl acetate polymer is very flexible. However, such a film has a highly tacky surface and thus practical film coating has been difficult unless a tackiness-reducing agent such as talc is added. In particular, the film coating of granules having an average particle size of 300 μm or less has been extremely difficult.

In recent years, as the society is rapidly aging, quick-disintegrating tablets in the buccal cavity which quickly disintegrates in saliva or in a small amount of water have been developed as the dosage form easily taken even by elderly and pediatric patients who have weak swallowing ability. Such a tablet has been contributing to enhanced convenience at medical practice sites and the patient compliance through ease of administration. However, the quick-disintegrating tablet in the buccal cavity has short history, and there are technical problems such as disintegrating time and mouthfeel in the buccal cavity and assuring the tablet hardness free from cracks and abrasion during the production and transportation. Consequently, it is demanded to develop technology for producing a quick-disintegrating tablet in the buccal cavity which has a suitable hardness, quick-disintegrating properties and enhanced mouthfeel by masking the bitter taste of a drug. Even higher achievement in the technology for producing a quick-disintegrating tablet in the buccal cavity is expected.

Patent Literature 1 discloses the film coating agent for a granule-containing tablet having sustained-release properties which gradually release a drug, but not for the purpose of masking the bitter taste of a drug.

Patent Literature 2 describes a quick-disintegrating tablet in the buccal cavity in which the bitter taste of a drug is masked. However, the method described in the literature is to produce a bitterness-masked drug-containing particle without coating a microcrystalline cellulose core particle with a drug, but by mixing a film coating liquid to a drug and a saccharide and then spray drying the obtained mixture. Further, Patent Literature 2 discloses a method for producing a tablet by mixing the resultant drug-containing particle and a saccharide.

Patent Literature 3 discloses a method for preventing the film damage caused during tableting by allowing a carbohydrate core particle to carry a drug and coating the particle with at least two film layers.

Patent Literature 4 discloses a method for producing a film-coated granule which releases a drug in a short time by allowing a spherical core particle to carry a drug and coating the particle with the film to mask the bitter taste.

PRIOR ART

Patent Literature

Patent Literature 1: WO 2009/011367
Patent Literature 2: WO 2002/02083
Patent Literature 3: JP 8-109126 A
Patent Literature 4: JP 2000-128776 A

SUMMARY OF THE INVENTION

Technical Problem to be Solved by the Invention

The technique described in Patent Literature 1 relates to the sustained-release function which gradually releases a drug, but not the immediate release function which releases a drug in a short time. Further, the literature simply describes a tablet containing film-coated granules, but does not include functions such as masking the bitter taste of a drug or quick-disintegrating tablet in the buccal cavity.

Furthermore, in the method described in Patent Literature 2, tableting is carried out at a low compression force so as not to impair the film properties in masking the bitter taste of a drug-containing particle. The tablet produced using a low compression force cannot assure the practical hardness. For this reason, the tablet hardness is assured by two-step drying of moistening-drying and low-temperature drying. Thus, the tablet hardness and the quick-disintegrating properties are assured by adjusting the conditions during the drying step in the production steps, but the formulation of the tablet and the coated granules for the tableting is not at all improved.

Patent Literature 3 discloses a coating technique using an impact resistant film by providing a film layer having a film softening temperature different from that of the enteric layer inside or outside, or both sides, of the enteric layer. In this method, the damage to the coating film caused during tableting is reduced by coating a granule for the tableting with a multilayer coating film. However, such a multilayer coating is inferior to a single-layer coating in the productivity and cost efficiency.

Further, Patent Literature 4 describes a technique by which a granule is coated with a film for masking the bitter taste, but does not mention a method for producing a tablet containing film-coated granules or a quick-disintegrating tablet in the buccal cavity or the application of the film-coated granules to a tablet.

As described above, up to date, the technology for producing the quick-disintegrating tablet in the buccal cavity having good masking properties for the bitter taste of a drug, quick dissolution properties and containing film-coated granules, which quickly disintegrates in the mouth has not been known.

Technical Solution to the Problem

To solve the above-mentioned problems, the present inventors have conducted intensive studies on the mixing formulation of a film coating liquid capable of masking the bitter taste of a drug, and found that the flexibility can be imparted and the bitter taste of a drug can be also masked by adding a flexible film coating liquid to a film coating liquid for the pharmaceutical solid preparations commonly used for masking the bitter taste, whereby the film-coated granules which release a drug in a short time is provided. Further, the present inventors have found that when the mixing ratio of both liquids is limited, the tensile elongation of the film, indicating the flexibility of a film, can be 150% or more and the tensile strength of the film, indicating the strength of a film, can be 9 N or more, and the granule comprising the elementary granule having the periphery thereof coated with a single layer of this film has little film damage, even when a compression force is applied from outside and the granule is deformed, thereby causing little fluctuation in the drug dissolution rate. Similarly, even when the compression force used for tableting is applied to the granules coated with this film to formulate a tablet, little damage is caused to the film and the drug dissolution pattern of said tablet is almost equal to the drug dissolution pattern of the granules coated with this film when the compression force is applied from outside.

Further, the drug dissolution rate of said granule is, to cope with a bitter tasting drug, suppressed to be 10% or less after 1 minute and 90% or more after 30 minutes. Thus, the dissolution rate is controlled so that the effect of immediate onset can be well expected while the drug dissolution rate at the initial stage is suppressed.

In the present application, the granules adhered to each other and agglomerated at the time of producing the film-coated granules are indicated as the agglomeration ratio. When the agglomeration ratio is suppressed to be 10% or less, the film-coated granules can be sufficiently produced at the typical production efficiency of pharmaceutical products.

Owing to the tablet containing film-coated granules in which the bitter taste of a drug is masked of the present application, the disintegrating solid preparation, more specifically, the tablet having suitable hardness and exhibiting the quick-disintegrating properties in the buccal cavity, can be easily obtained without undergoing cumbersome production steps. The film-coated granule and the tablet of the present invention have the bitter taste of a drug masked, and are the quick-soluble film-coated granule and the tablet which release a drug in a short time.

Further, the present inventors have found that carbohydrate trehalose, microcrystalline cellulose, a disintegrant and a lubricant are suitable as other component compositions used for the disintegrating solid preparation containing film-coated granules in which the bitter taste of a drug is masked. The carbohydrate trehalose and the microcrystalline cellulose are mixed and granulated together in advance and adjusted to be granulated granules having an average particle size of 50 to 400 μm. The film-coated particles in which the bitter taste of a drug is masked, a disintegrant and a lubricant are mixed with the obtained granulated granules and the resultant mixture is subjected to tableting, thereby obtaining the quick-disintegrating tablet in the buccal cavity which exhibits quick disintegration in the buccal cavity and in which the bitter taste of a drug is masked.

Furthermore, when the carbohydrate is limited to trehalose and the mixing ratio with the microcrystalline cellulose is limited within a certain range, the quick-disintegrating tablet having a high hardness can be obtained applying an even low compression force without damaging the film of the film-coated granule in which the bitter taste of a drug is masked. When mannitol, which is also a carbohydrate, is used in place of trehalose, the moldability is deteriorated and a high compression force is required, consequently impairing the disintegrating properties of the tablet, thereby failing to obtain the quick-disintegrating tablet.

The quick-disintegrating tablet in the buccal cavity which has the desired suitable hardness and exhibits quick-disintegrating properties in the buccal cavity can be obtained by an easy method in which the above-mentioned components are mixed and the mixture is subjected to tableting, without using any special manufacturing machines, but by using a typical granulator and a tableting machine and molded into a tablet.

More specifically, the present invention is as follows.

(1) A coating film comprising Component A: an ethyl cellulose and Component B: an ethyl acrylate/methyl methacrylate copolymer or a plasticized vinyl acetate polymer, and having a tensile elongation of 150% or more and a tensile strength of 9 N or more.

(2) The coating film according to (1), further comprising Component C: a pharmaceutical additive, Component D: a plasticizer, and Component E: an inorganic substance.

(3) The coating film according to (2), wherein the mass ratio of the Components A:B:C:D:E is 100:(100 to 300):(6 to 90):(6 to 90):(30 to 90).

(4) The coating film according to (2) or (3), wherein the Component C: a pharmaceutical additive is a polyvinyl alcohol copolymer or a methyl methacrylate/butyl methacrylate/dimethylaminoethyl methacrylate copolymer.

(5) The coating film according to (2) or (3), wherein the Component D: a plasticizer is triethyl citrate.
(6) The coating film according to (2) or (3), wherein the Component E: an inorganic substance is titanium oxide.
(7) A granule comprising a drug-containing elementary granule having the periphery thereof coated with a coating film, and having a drug dissolution rate of 10% or less in 1 minute and 90% or more in 30 minutes, and further an agglomeration ratio of 10% or less.
(8) The granule according to (7), wherein the coating film is a coating film according to any of (1) to (6).
(9) The granule according to (7) or (8), wherein the granule coating film, has only a single layer and a drug dissolution rate when a compression force of maximum 25 kN is applied to the granule is within ±10% of a drug dissolution rate of the granule to which a compression force is not applied.
(10) The granule according to (9), wherein the elementary granule contains a spherical core particle containing 70% by mass or more of a microcrystalline cellulose.
(11) A tablet containing 0.55 to 90.0% by mass of the granule according to any of (7) to (10).
(12) The tablet according to (11), further containing trehalose, a microcrystalline cellulose, a disintegrant and a lubricant.
(13) The tablet according to (12), wherein the mass ratio of granule:trehalose:microcrystalline cellulose:disintegrant:lubricant is 100:(30 to 6900):(12 to 3000):(0.1 to 1000):(0.1 to 1000).

Advantageous Effects of Invention

An advantageous effect of the present invention is to be able to efficiently produce a film-coated granule in Which the bitter taste of a drug is masked and having little dissolution fluctuation affected by the tableting. Further, the tablet containing the film-coated granules in which the bitter taste of a drug is masked provides the quick-disintegrating tablet in the buccal cavity which has suitable hardness, is fee of the bitter taste even when quickly disintegrating in the buccal cavity, releases a drug in a short time after taken, and is easy to be taken for elderly people, infants and patients having difficulty in swallowing. Furthermore, said tablet can be easily obtained without undergoing cumbersome production steps.

The film coating liquid of the present invention is to suppress the bitter taste of a drug and be applied to the extent that the bitterness of a drug is not tasted when the tablet disintegrates in the buccal cavity.

DESCRIPTION OF EMBODIMENTS

Figure 1:
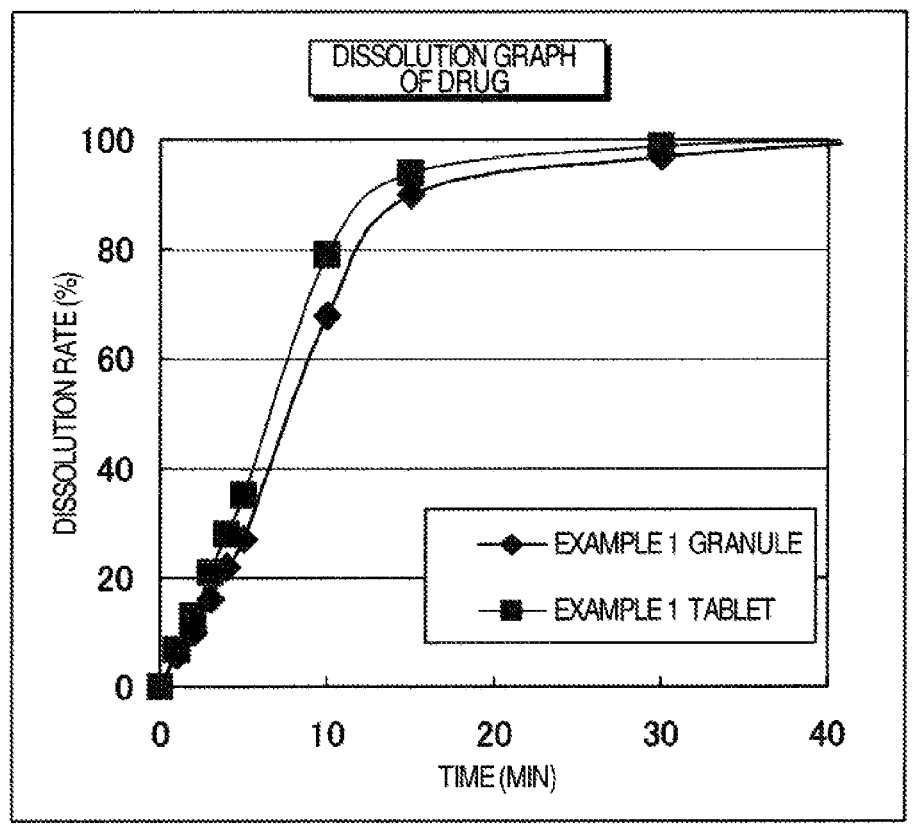
FIG. 1 is the in vitro drug dissolution profiles of the film-coated granules and the tablet containing the film-coated granules of Example 1.

The present invention is described specifically below.
The film of the present invention comprises Component A: an ethyl cellulose and Component B: an ethyl acrylate/methyl methacrylate copolymer or a plasticized vinyl acetate polymer.
Component A: an ethyl cellulose is generally used for film coating agents for pharmaceutical solid preparations, and commercial products such as Aquacoat ECD30 (FMC) and Surelease (Colorcon) can be used.
Component B: an ethyl acrylate/methyl methacrylate copolymer is an emulsion of a copolymer resin obtained by polymerizing ethyl acrylate and methyl methacrylate in water using polyoxyethylene nonylphenyl ether as an emulsifier and comprises a small amount of dimethylpolysiloxane. The solid content thereof is about 30% by mass. Specifically, the ethyl acrylate/methyl methacrylate copolymer should meet the standards of "ethyl acrylate/methyl methacrylate copolymer dispersion" in Japanese Pharmaceutical Excipients Standards 2003, and commercial products such as Eudragit NE30D (Degussa), Kollicoat EMM30D (BASF), and the like are used.
A plasticized vinyl acetate polymer is an aqueous dispersion of vinyl acetate resin fine particles (about 27% by mass) containing a vinyl acetate polymer comprising 2.5% povidone and 0.3% sodium lauryl sulfate. An example of the commercial product is one in which a plasticizer (triethyl citrate, propylene glycol, and the like) in about 15% by mass with respect to the solid content of the aqueous dispersion is added to Kollicoat (registered trademark) SR30D (BASF).
The film of the present invention is required to have a tensile elongation of 150% or more and a tensile strength of 9 N or more. The tensile elongation and the tensile strength are values represented by the tensile elongation and the tensile strength of a cast film, respectively, to be described later (Examples). When the tensile elongation is 150% or more and the tensile strength is 9 N or more, the film is not damaged by a compression force during tableting and the dissolution properties does not change.

The tensile elongation is preferably 200 to 800%, and more preferably 300 to 800%. The tensile strength is preferably 10 to 300 N, and more preferably 11 to 300 N.

The film of the present invention preferably further comprises Component C: a pharmaceutical additive, Component D: a plasticizer and Component E: an inorganic substance, in addition to Component A: an ethyl cellulose and Component B: an ethyl acrylate/methyl methacrylate copolymer or a plasticized vinyl acetate polymer.

Component C: a pharmaceutical additive is selected from the additives listed in the Japanese Pharmaceutical Excipients Standards, and is preferably one or two or more of polyvinyl alcohol copolymer (e.g., trade name "PVA copolymer (POVACOAT)"), methyl methacrylate/butyl methacrylate/dimethylaminoethyl methacrylate copolymer (e.g., trade name "aminoalkyl methacrylate copolymer E (Eudragit EPO)", hydroxypropylcellulose (e.g., trade name "HPC"), hydroxypropylmethyl cellulose (e.g., trade name "hypromellose"), polyvinylpyrrolidone (e.g., trade name "povidone"), lactose, sucrose, mannitol, trehalose, sorbitol, and the like. More preferable are polyvinyl alcohol Copolymer (e.g., trade name "PVA copolymer (POVACOAT)"), and methyl methacrylate/butyl methacrylate/dimethylaminoethyl methacrylate copolymer (e.g., trade name "aminoalkyl methacrylate copolymer E (Eudragit EPO)"). They dissolve quickly in water and the tackiness of the solution does not increase even when they dissolve, and hence they are suitable as pharmaceutical additives for the coating film.

Component D: a plasticizer is a substance which imparts the plasticity to a high molecular weight substance, and typically reduces the glass transition point and the softening temperature. Specific examples of the plasticizer include those listed in Japanese Pharmaceutical Excipients Standards such as triethyl citrate, triacetin, glycerol, dibutyl phthalate, propylene glycol, dimethyl sebacate, medium chain triglyceride, acetyl triethyl citrate, tributyl citrate, acetyl tributyl citrate, dibutyl adipate, oleic acid, and oleinol. Since the selection of the plasticizer largely depends on the drug dissolution properties and preparation design (drug dissolution rate, storage stability), the plasticizer is selected based on the correlation between a drug and the film properties. Among these, preferable is triethyl citrate, which does not break the polymer when it is added to Component A: an ethyl cellulose and Component B: an ethyl acrylate/methyl methacrylate copolymer or a plasticized vinyl acetate polymer, hence making it possible to impart the optimum film plasticity (tensile elongation and tensile strength).

Component E: an inorganic substance is selected from the additives listed in Japanese Pharmaceutical Excipients Standards, and titanium oxide, talc, light anhydrous silicic acid, synthetic aluminum silicate, calcium stearate, magnesium stearate, silicon dioxide, magnesium aluminometasilicate, and the like, are used. Among these, preferable is titanium oxide because if has a small particle size and hence does not affect the film properties even when interspersed in the film. Further, titanium oxide has a large specific gravity and thus has good dispersibility in the film coating liquid and operability. Commonly, talc is used for the purpose of reducing the tackiness but, in the present formulation, titanium oxide exhibits extremely good performance in regard to tackiness reduction, strength enhancement, workability improvement at the time of film coating (the reduction of a deposited amount to the interior wall of an equipment by static electricity.)

Titanium oxide refers to titanium dioxide ($TiO_2$) and are those which meet the standard of "titanium oxide" in the Japanese Pharmacopoeia, Fifteenth Edition (hereinafter, JP), Commercial products such as KA-10 (Titan Kogyo, Ltd.) and titanium oxide (TOHO TITANIUM CO., LTD.) are available.

The film composition containing the above Components (A) to (E) contains Component (A): an ethyl cellulose, Component (B): an ethyl acrylate/methyl methacrylate copolymer or a plasticized vinyl acetate polymer, Component (C): a pharmaceutical additive, Component (D): a plasticizer and Component (E): an inorganic substance in the mass ratio of preferably 100:(100 to 300):(6 to 90):(6 to 90):(30 to 90), more preferably 100:(100 to 250):(10 to 70):(10 to 50):(30 to 80), and further preferably 100:(100 to 200):(10 to 50):(10 to 30):(30 to 70).

When (B): an ethyl acrylate/methyl methacrylate copolymer or a plasticized vinyl acetate polymer is 100 or more per 100 of (A): an ethyl cellulose, the elongation and strength of the film are good. When (B): an ethyl acrylate/methyl methacrylate copolymer or a plasticized vinyl acetate polymer is 300 or less per 100 of (A): an ethyl cellulose, the film tackiness is reduced and the agglomeration of granules after the film coating is less likely to occur. When (C): a pharmaceutical additive is 6 or more per 100 of (A): an ethyl cellulose, the drug dissolution rate is increased, resulting in good quick solubility. When (C): a pharmaceutical additive is 90 or less per 100 of (A): an ethyl cellulose, the drug dissolution rate can be suppressed and the bitterness of a drug is not tasted in the buccal cavity, providing good masking effect on the bitter taste.

The granules coated with the film of the present invention must have the suitable drug dissolution pattern immediately after the production of said granules, and the pattern must not greatly change during the storage. To achieve it, the pattern is more stable when the film is thicker, and hence the film thickness is preferably 10 μm or more, more preferably 15 μm or more, and further preferably 20 μm or more. However, when an amount of the film coating is simply increased, the drug dissolution rate is reduced and a drug is not at all released in an extreme case. For this reason, it is desirable that the components should be used in the above mixing range to attain a target film coating amount (film thickness) and dissolution pattern.

The film-coated granules of the present invention preferably has only a single film layer, and the compression force during tableting ranges preferably within 0.1 to 25 kN. With the force within this range, the film is not damaged and the drug dissolution rate is within ±10% of a drug dissolution rate of the granule to which a compression force is not applied, thus being substantially free of the change in the drug dissolution rate.

The compression force is the force required to mold a tablet, and is more preferably 0.1 to 20 kN and further preferably 0.1 to 15 kN in consideration of tableting machine deterioration and load on the film.

When (D): a plasticizer is 6 or more per 100 of (A): an ethyl cellulose, the glass transition point of (A) an ethyl cellulose is suitably reduced and the film forming property is not affected. When (D): a plasticizer is 90 or less per 100 of (A): an ethyl cellulose, the film does not excessively soften and the tackiness is reduced, and hence is most suitable as the film.

When (E): an inorganic substance is 30 or more per 100 of (A): an ethyl cellulose, the film-tackiness reducing effect is enhanced, thus reducing the granule agglomeration after coating. When (E): an inorganic substance is 90 or less per 100 of (A): an ethyl cellulose, the inorganic substance is suitably interspersed in the film, thereby maintaining the elongation and the strength of the film.

The coating liquid for forming the film of the present invention preferably has a solid component concentration, other than water, of 5.0% to 50.0% by mass, more preferably 5.0 to 35.0% by mass, and further preferably 10.0 to 30.0% by mass.

As described earlier, when Component B: an ethyl acrylate/methyl methacrylate copolymer or a plasticized vinyl acetate polymer having flexibility is added to Component A: an ethyl cellulose, flexibility can be imparted, and when the mixing ratio of both solutions is limited, the tensile elongation, indicating the flexibility of the film, can be 150% or more and the tensile strength, indicating the strength of the film, can be 9 N or more. In addition, strength can be imparted. Further, when Component C: a pharmaceutical additive which quickly dissolves in water is added thereto, the tackiness of the solution does not increase even when it dissolves, enabling the drug dissolution rate to be controlled. Furthermore, when Component (D): a plasticizer and Component (E): an inorganic substance are added thereto, the tackiness can be reduced and the strength can be enhanced while maintaining the flexibility.

The above film is prepared, for example, by the procedures of (1) adding Component D: a plasticizer to pure water while stirring with a propeller, stirring the mixture for about 10 minutes, then adding Component A: an ethyl cellulose thereto, and stirring the mixture for about 10 minutes. (2) Further adding Component C: a pharmaceutical additive and Component E: an inorganic substance thereto while continuing stirring and stirring the mixture for about 15 minutes, (3) further adding Component B: an ethyl acrylate/methyl methacrylate copolymer (or a mixed solution of a plasticizer and vinyl acetate polymer mixed in advance) and gently stirring the mixture for about 10 minutes, and (4) passing the resulting mixture through a sieve having a sieve opening of 250 μm.

Component A: an ethyl cellulose does not form a film without a plasticizer, but acts as a tackiness-reducing agent with very high suspension stability in the present invention.

The granule obtained by coating an elementary granule (a particle containing a drug) with the of the present invention disclosed in the present application by a known method is a preferred embodiment.

The elementary granules may be those prepared by high-speed stirring granulation, fluidized-bed granulation, extrusion granulation, extrusion/spheronization granulation method, or drug layering method using core particles, or may be drug crystalline particles. However, in order to make the film-coated granule of which dissolution rate is to be precisely controlled, spherical granules prepared using the layering method is the most suitable.

The size of the elementary granules may be determined in accordance with the preparation design idea, but the smaller elementary granule is desired for further tableting. The reason is that the smaller elementary granule is effective in suppressing the damage on the film caused by mechanical stress at the time of tableting and also suppressing the segregation (variation in the mixing components ratio) during the mixing of the powder for tableting and the transportation as well as during tableting. Specifically, the elementary granule has an average particle size of preferably 50 μm or more and 300 μm or less, and further preferably 50 μm or more and 200 μm or less. The average particle size herein refers to a value at a cumulative 50% by mass in the cumulative distribution under sieve of particle sizes determined by a sieving method.

The drug dissolution rate after 1 minute of the granule in which the elementary granule is coated with the film of the present invention, in the case of a bitter tasting drug, must be suppressed. When the drug dissolution rate after 1 minute is 10% or less, the bitterness of any drug, although depending on the degree of bitterness, is at the level of being tasteless, and hence it is preferable. Further, as the level of quick drug dissolution, the dissolution rate of 90% or more after 30 minutes is considered quicksolubility, and hence it is preferable.

The agglomeration ratio of the above granules indicates the percentage of the granules adhered to each other and agglomerated under the influence of the film tackiness at the time of preparing the film-coated granules. The agglomerated granules impair the intended dissolution control function and thus must be removed. The agglomeration of the granules leads to reduction in the production efficiency. Typically, the agglomeration ratio is preferably 10% or less, and more preferably 5% or less, in viewpoint of the production efficiency of pharmaceutical products. Further, the tackiness of the film alone can also be evaluated by the value based on the touch of the film surface with a fingertip, and such a value is used as a criterion to assess the practical production efficiency. Thus, to attain such physical properties, the solid component weight ratio of the film composition components is suitably adjusted as described above.

The spherical core particle used in the drug layering method is pharmaceutical inert, more specifically, does not contain a drug, and comprises microcrystalline cellulose, lactose, sucrose, mannitol, cornstarch, powdered cellulose, calcium hydrogen phosphate, calcium carbonate, low-substituted hydroxypropylcellulose, carmellose calcium, pregelatinized starch, partly pregelatinized starch, croscarmellose sodium, crospovidone, carboxymethyl starch, hydroxypropylcellulose, povidone, xanthan gum, or the like. Among those, the use of microcrystalline cellulose spherical core particles causes little agglomeration of granules while layering. The spherical core particle contains preferably 70% by mass or more, and further preferably 80% by mass or more of microcrystalline cellulose. An example of the microcrystalline cellulose spherical core particle is CELPHERE (registered trademark) (Asahi Kasei Chemicals Corporation).

The method for producing the elementary granules according to the drug layering method using the spherical core particles is described. The layering method, to the core particles, includes a method for coating by concurrently supplying a drug powder and an aqueous binder solution, a method for coating by supplying a suspension of drug particles, a method for coating by supplying an aqueous drug solution, and the like. In the case of the method for coating by concurrently supplying a drug powder and an aqueous binder solution, an additive other than a drug, for example, an excipient is used by mixing with the drug powder as necessary. When a drug suspension or an aqueous solution is used, a fluidized-bed coating apparatus (sometimes referred to as fluidized-bed drier or fluidized-bed granulator) is suitably used.

Usable fluidized-bed coating apparatuses include, in addition to the common fluidized-bed type, a spouted bed type having a guide tube (Wurster column) inside thereof, a tumbling fluidized bed type equipped with a rotation mechanism on the bottom thereof, and the like. Examples of the apparatus include "FLO-COATER" (trade name) and "SPI- RAL-FLOW" (trade name) manufactured by Freund Corporation, "WST/WSG series" and "GPCG Series" manufactured by Glatt GmbH, "New Marumerizer" (trade name) manufactured by Fuji Paudal Co., Ltd., and "Multiplex" (trade name) manufactured by Powrex Corporation and the like. The layering liquid can be supplied by selecting a method suited for each of the apparatuses from top spray, bottom spray, side spray and tangential spray, and spraying to the core particles continuously or intermittently. The above apparatuses are preferably used since even smaller core particles can be produced with less agglomeration.

The elementary granules contain typically at least 0.01% by mass of a drug. The drug used in the present invention refers to the one used for treatment, prevention or diagnosis of human or animal diseases but excludes instruments and machines. Examples include anti-epileptic agents (such as phenytoin, acetylpheneturide, trimethadione, phenobarbital, promidone, nitrazepam, sodium valproate and sultiame), antipyretic, analgestic and anti-inflammatory agents (such as acetaminophen, phenyl acetylglycine methyl amide, mefenamic acid, diclofenac sodium, floctafenine, aspirin, aspirin aluminum, ethenzamide, oxyphenbutazone, sulpyrin, phenylbutazone, ibuprofen, alclofenac, naproxen, ketoprofen, tinoridine hydrochloride, benzydamine hydrochloride, tialamide hydrochloride, indomethacin, piroxicam, and salicylamide), antivertigo agents, for example, dimenhydrinate, meclizine hydrochloride, and difenidol hydrochloride), narcotics (such as opium alkaloids hydrochlorides, morphine hydrochloride, codeine phosphate, dihydrocodeine phosphate, and oxymethebanol), agents for psychological use (such as chlorpromazine hydrochloride, levomepromazine maleate, perazine maleate, propericiazine, perphenazine, chlorprothixene, haloperidol, diazepam, oxazepam, oxazolam, mexazolam, alprazolam, and zotepine), skeletal muscle relaxants (such as chlorzoxazone, chlorphenesin carbamate, chlormezanone, pridinol mesylate, and eperisone hydrochloride), autonomic nerve agents (such as betanecol chloride, neostigmine bromide, and pyridostigmine bromide), antispasmodic agents (such as atropine sulfate, butropium bromide, butylscopolamine bromide, propantheline bromide, and papaverine hydrochloride), antiparkinsonian agents (such as biperiden hydrochloride, trihexyphenidyl hydrochloride, amantadine hydrochloride, and levodopa), antihistamine agents (such as diphenhydramine hydrochloride, dl-chlorpheniramine maleate, promethazine, mequitazine, and clemastine fumarate), cardiotonic agents (such as aminophylline, caffeine, dl-isoproterenol hydrochloride, etilefrin hydrochloride, norfenerine hydrochloride, and ubidecarenone), antiarrhythmic agents (such as procainamide hydrochloride, pindolol, metoprolol tartrate, and disopyramide), diuretics (such as potassium chloride, cyclopenthiazide, hydrochlorothiazide, triamterene, acetazolamide, and furosemide), antihypertensive agents (such as hexamethonium bromide, hydralazine hydrochloride, syrosingopine, reserpine, propranolol hydrochloride, captopril, and methyldopa), vasoconstrictor agents (such as dihydroergotamine mesylate), vasodilatory agents (such as etafenone hydrochloride, diltiazem hydrochloride, carbochromen hydrochloride, pentaerythritol tetranitrate, dipyridamole, isosorbide nitrate, nifedipine, nicametate citrate, cyclandelate, and cinnarizine), agents for arteriosclerosis (such as ethyl linoleate, lecithin, and clofibrate), agents for the circulatory organs (such as nicardipine hydrochloride, meclofenoxate hydrochloride, cytochrome C, pyridinol carbamate, vinpocetine, calcium hopantenate, pentoxifylline, and idebenone), respiratory stimulants (such as dimefline hydrochloride), antitussives and expectorants (such as codeine phosphate, dihydrocodeine phosphate, dextromethorphan hydrobromide, noscapine, methyl L-cysteine hydrochloride, bromhexine hydrochloride, theophylline, ephedrine hydrochloride, and anlexanox), cholagogues (such as osalmid, phenyl propanol, and hymecromone), agents for intestinal disorders (such as berberine chloride, and loperamide hydrochloride), agents for digestive organs (such as metoclopramide, fenipentol, and domperidone), vitamin preparations (such as retinol acetate, dihydrotaehysterol, etretinate, thiamine hydrochloride, thiamine nitrate, fursultiamine, octotiamine, cycotiamine, riboflavin, pyridoxine hydrochloride, pyridoxal phosphate, nicotinic acid, pantethine, cyanocobalamin, biotin, ascorbic acid, phytonadione, and menatetrenone), antibiotics (such as benzathine benzylpenicillin, amoxicillin, ampicillin, cyclacillin, cefaclor, cephalexin, cefuroxime axetil, erythromycin, kitasamycin, josamyera, chloramphenicol, tetracycline, griseofulvin, and cefuzonam sodium), and chemotherapeutic agents (such as sulfamethoxazole, isoniazid, ethionamide, thiazosulfone, nitrofurantoin, enoxacin, ofloxacin, and norfloxacin).

The elementary granules are film-coated using the same apparatus as in the drug layering method. Preferably usable fluidized-bed apparatuses are a spouted bed type having a guide tube (Wurster column) inside thereof and a tumbling fluidized bed type equipped with a rotation mechanism on the bottom thereof. A film coating liquid can be supplied by selecting a method suited for each of the apparatuses from top spray, bottom spray, side spray and tangential spray, and spraying to the elementary particles. During spraying, the film coating liquid is constantly stirred with a propeller and the like, so as not to precipitate an inorganic substance in the film coating liquid. After completion of spraying, the resulting film-coated granules are allowed to stand to dry or dried after adjusting the air flow and temperature as necessary, without taking out the samples from the apparatus. It is preferable to further carry out heat treatment (curing) since film forming property is increased.

The film-coated granules collected from the apparatus were calculated for the mass percentage of the collected film-coated granules with respect to the total charge mass, thereby determining a collection ratio. The collection ratio is typically preferably 80% or more, and more preferably 90% or more, since it affects the production efficiency of the product.

The tablet containing the granules coated with the film of the present invention, preferably the quick-disintegrating preparation in the buccal cavity, more specifically the quick-disintegrating tablet in the buccal cavity, refers to a pharmaceutical preparation which can be taken without water, is free of the bitter taste in the buccal cavity, and disintegrates within 90 seconds, more preferably within 60 seconds, and further preferably within 30 seconds as the tablet disintegration time measured in accordance with General Tests, "Disintegration Test" in the Japanese Pharmacopoeia, Fifteenth Edition.

Further, in the disintegration test in the buccal cavity in which the tablet is actually placed in the mouth of a human and disintegrated only by saliva, the tablet disintegrates preferably within 60 seconds, and more preferably within 30 seconds.

The above-mentioned tablet contains 0.55 to 90% by mass of the above-mentioned film-coated granules, and preferably further contains trehalose, a microcrystalline cellulose, a disintegrant and a lubricant.

The above-mentioned tablet, preferably the quick-disintegrating preparation in the buccal cavity, and more specifically, the quick-disintegrating tablet in the buccal cavity, may contain other components than trehalose, a microcrystalline cellulose, an active component, a disintegrant and a lubricant. Examples of such components include other excipients, disintegrants, binders, plasticizers, lubricants, flavoring agents, perfumes, coloring agents, sweeteners, surfactants and the like. Examples of the excipient include saccharides such as sucrose, glucose, lactose, fructose, and maltose, sugar alcohols such as xylitol, maltitol, and sorbitol, starches such as rice starch, wheat starch, corn starch, and potato starch, and inorganic substances such as dibasic calcium phosphate, calcium carbonate, silicic anhydride, hydrated silicate, aluminium silicate, and magnesium aluminosilicate.

Examples of the binder include water-soluble polysaccharides such as gelatin, pullulan, carrageenan, xanthan gum, tamarind gum, pectin, sodium alginate, and gum arabic, celluloses such as hydroxypropylcellulose, hydroxypropylmethyl cellulose, and methyl cellulose, starches such as pregelatinized starch, partly pregelatinized starch, and starch paste, and synthetic polymers such as polyvinyl pyrrolidone, carboxy vinyl polymer, and polyvinyl alcohol.

Examples of the plasticizer include hydrated silicon dioxide and light anhydrous silicic acid.

Examples of the flavoring agent include glutamic acid, fumaric acid, succinic acid, citric acid, sodium citrate, tartaric acid, malic acid, ascorbic acid, sodium chloride, and 1-menthol.

Examples of the perfume include orange, vanilla, strawberry, yogurt, and menthol.

Examples of the coloring agent include food coloring agents such as Food Red No. 3, Food Yellow No. 5, and Food Blue No. 1, and riboflavin.

Examples of the sweetener include aspartame, saccharin, dipotassium glycyrrhizate, and stevia. Examples of the surfactant include phospholipid, glycerol esters of fatty acids, polyethylene glycol fatty acid ester, sorbitan fatty acid ester, and polyoxyethylene hydrogenated castor oil.

The trehalose used in the present invention is an irreducible disaccharide formed by an α-1,1-glucosidic bond and odorless white crystalline or non-crystalline powder with sweet taste. Commercial products such as Trehalose G, SG (Hayashibara Biochemical Laboratories, Inc.), and Trehalose P, G (Asahi Kasei Chemicals Corporation) can be used.

The microcrystalline cellulose used in the present invention is white microcrystalline powder prepared by partially depolymerizing α-cellulose obtained from a fibrous plant in the form of pulp by using a mineral acid and purifying the resultant product. Further, while there are a wide variety of the grades of microcrystalline cellulose, the microcrystalline cellulose in the present invention preferably has a bulk density, a physical property of highly moldable microcrystalline cellulose powders, of 0.2 g/ml, an average particle size of 50 μm, an angle of repose of 50°, and a ratio of the major axis to minor axis (L/D) of the average particle size of 2.5 to 4.0. Commercial products such as Ceolus KG-802 (trade name) and Ceolus UF-711 (trade name) (Asahi Kasei Chemicals Corporation) can be used.

Examples of the disintegrant used in the present invention include potato starch, corn starch, partly pregelatinized starch, pregelatinized starch, starches, sodium starch glycolate, carboxymethyl cellulose calcium, low-substituted hydroxypropylcellulose, carboxymethyl cellulose, crospovidone, carmellose, carmellose sodium, carmellose calcium and the like. Crospovidone (Polyplasdone XL-10: ISP), partly pregelatinized starch (PCS PC-10: Asahi Kasei Chemicals Corporation), and pregelatinized starch (SWELSTAR PD-1, FD-1; Asahi Kasei Chemicals Corporation) are more preferable.

Examples of the lubricant used in the present invention include talc, magnesium stearate, calcium stearate, sucrose fatty acid ester, polyglycerol esters of fatty acids and the like. Talc is more preferable. The talc is white to grayish white color microcrystalline powder and contains natural hydrated magnesium silicate and a small amount of aluminum silicate. Commercial products such as TALCAN HAYASHI (trade name) (HAYASHI KASEI CO., LTD.) and talc (Nippon Talc Co., Ltd., FUJI TALC INDUSTRIAL CO., LTD., Oriental Pharmaceutical Co., Ltd., Tsuchiya Kaolin Industry Ltd.) can be used.

Essentially, the lubricant is added for the purpose of preventing the powder from adhering to the die and punch when tableting a tablet, but when the lubricating effect is too strong, the tablet moldability is deteriorated, thereby requiring the application of a high pressure to attain the practical tablet hardness of 40 to 60 N. For the tablet produced under a high pressure, the disintegration rate of the tablet tends to delay, and hence it is not suitable for the disintegrating tablet in the buccal cavity. Thus, the tableting needs to be carried out under a pressure as low as possible.

The tablet hardness is expressed as the hardness level of the tablet, and is preferably 40 to 120 N to prevent the tablet from cracking and breaking during transportation and storage. In most cases, the hardness and disintegration time are in the proportional relation. Thus, for the disintegrating tablet in the buccal cavity which requires short disintegration time, the tablet hardness is more preferably 40 to 80 N, and further preferably 40 to 60 N.

Further, the abrasion test (carried out in accordance with General Rules for Preparations in the Japanese Pharmacopoeia, Fifteenth Edition) to test the tablet hardness is determined by charging a rotary disk with tablets, allowing the disk to rotate for a certain period of time, and calculating the mass percentage of cracked, broken or powdered tablets. The abrasion level is preferably 0.5% or less, more preferably 0.3% or less, and further preferably 0.2% or less.

For the tablet composition allowing disintegration of the tablet within 60 seconds in the buccal cavity, the above-mentioned tablet preferably contains granule:trehalose:microcrystalline cellulose:disintegrant:lubricant in the mass ratio of 100:(30 to 6900):(12 to 3000):(0.1 to 1000):(0.1 to 1000). The tablet contains more preferably 0.55 to 90.0% of the granule, and further preferably 1.0 to 70.0% of the granule.

The mass ratio of the granule and the disintegrant is preferably 100:(0.1 to 1000). The mass ratio of the disintegrant in the whole tablet is preferably 0.1 to 10.0%, and more preferably 1.0 to 7.0%. The disintegrant is added for the purpose of facilitating the tablet disintegration and needs to be suitably adjusted since the fluidity and moldability of the disintegrant alone result in the nonuniform weight of the tablet and reduced hardness of the tablet.

The mass ratio of the granule and the lubricant is preferably 100:(0.1 to 1000). However, as described earlier, the amount of the lubricant added is in proportion to the lubricating effect, and thus the mass ratio of the lubricant in the whole tablet is preferably 0.1 to 5.0%, and more preferably 0.1 to 3.0%.

The mass ratio of the trehalose and the microcrystalline cellulose is, from viewpoints of the tablet hardness, disintegration properties, sweet taste and texture in the buccal cavity, preferably trehalose:microcrystalline cellulose=100.0:(11.1 to 100.0), and more preferably 100.0:(25.0 to 70.0). When the mass ratio of the microcrystalline cellulose is 100.0% by mass or less with respect to the trehalose, the tablet, when administered, has good feel on the tongue in the buccal cavity and enough sweetness, hence preferable as a disintegrating tablet in the buccal cavity. When the mass ratio of the microcrystalline cellulose is 11.1% by mass or more, the tablet has good moldability and does not require a high pressure during tableting, hence preferable as a disintegrating tablet in the buccal cavity.

The mixed powder is granulated to obtain granulated granules with the trehalose and the microcrystalline cellulose in the mass ratio of trehalose:microcrystalline cellulose=100.0:(11.1 to 100.0). For the mixing method, a method is typically used in which the apparatuses commonly used for the production of pharmaceutical products are used, and examples of the apparatus include V-shape mixer, double cone mixer, tumbler mixer (DALTON CO., LTD.) and the like. For the granulating method, water is added or sprayed to the mixed powder running in a granulator, thereby producing granulated granules. Examples of the granulating apparatus include fluidized-bed granulator (Freund Corporation), high-speed stirring granulator (Powrex Corporation) and the like. The method for drying the granulated granules include fan drying, hot air drying and the like, and examples of the drying apparatus include fluidized-bed dryer (FLO-CAOTER (trade name); Freund Corporation, Multiplex (trade name); Powrex Corporation), box-type hot air circulation dryer, tray dryer and the like.

To make the size of granules uniform, the dried granulated granules are prepared, so that the average particle size is preferably 50 to 400 μm, and further preferably 50 to 300 μm, using a particle size selector. Examples of the particle size selector include oscillator, Comil and the like.

The disintegrant is added for the purpose of enhancing the tablet disintegrating properties, and may be granulated together with other drugs and excipients at the granulation stage, or may alternatively be added to the granulated granules. The amount of the disintegrant to be added is preferably 0.1 to 20.0% by mass, and former preferably 0.1 to 10.0% by mass, with respect to the tablet weight. When the additive amount of disintegrant is 20.0% by mass or less, the moldability of the tablet is less affected, hence preferable.

In the method of the tableting for producing the quick-disintegrating tablet in the buccal cavity, the mixed powder is fed, compressed and molded to produce a tablet, and an example of the tableting apparatus typically include a rotary tablet press (LIBRA 2 (trade name); Kikusui Seisakusho Ltd.). The feeder part from which the powder is supplied to the die can be selected from feeder types such as stirring feeder and open feeder in accordance with the powder fluidity and the granule size.

EXAMPLES

The present invention is described based on Examples.
The methods and conditions for measuring physical properties used in the present invention are as follows.
First, the methods for measuring physical properties are collectively described below.
<Tackiness, Tensile Strength and Tensile Elongation of Cast Film>
(1) A film coating liquid is poured in a plastic petri dish having a diameter of 8.5 cm in an appropriate amount (so as to have a thickness of a cast film in the range of 0.27 to 0.37 mm. When the concentration of the solid components other than water in the film coating liquid is 17% by mass, the amount is 11.3 g or so.).
(2) The sample is dried at 40° C. in an oven without air circulation for 10 hours.
(3) Immediately after taking out the dried sample from the oven, tackiness (stickiness) is evaluated by touching the film surface with a fingertip (washed well with soap and dried enough in advance). The evaluation criteria of the tackiness (4-grade evaluation) and the coating property corresponding thereto were examined and the following correlation was found.

1 None: spraying is possible at a comparatively high rate (minor agglomeration)
2 Minor: coating is possible when reducing the spray rate (some agglomeration)
3 Weak: coating is barely possible with an intermittent spray (much agglomeration)
4 Strong: agglomeration is observed at once and coating is not possible
(4) The petri dish is further heat-treated at 80° C. in an oven without air circulation for 1 hour.
(5) The petri dish is cooled to room temperature, and thereafter the film is peeled off and cut out into a rectangle sized 10 mm×30 mm.
(6) The cast film is set on a tensile tester (creep meter, RE-33005 (adaptor for a sheet tensile test, using 200 N loadcell). Yamaden Co., Ltd.) so as to have a spacing of measurement points of the tensile test for 10 mm and pulled at a rate of 0.5 mm/sec. The elongation (mm) and the strength (tensile strength) [N] on breaking the film are obtained.
(7) Tensile elongation [%] (=100× Elongation (mm)/10 (mm)) is calculated.
<Average Particle Size [μm] of Film-Coated Granules, Elementary Granules, Core Particles>
The particle size distribution is measured with a RoTap sieve shaker (Sieve Shaker Type A, manufactured by Hirako Seisaku-sho Co., Ltd.) by screening 10 g of the sample using a JIS standard sieve for 15 minutes. The particle size of 50% by mass cumulated in the cumulative distribution under sieve is defined as an average particle size.
<Collection Ratio [%] of Elementary Granules and Film-Coated Granules>
The collection ratio is determined by dividing the collection amount of elementary granules or film-coated granules by the total amount of raw materials employed and is represented as % by mass.
<Agglomeration Ratio [%] of Elementary Granules and Film-Coated Granules>
Agglomerated products (coarse particles: granule particle size of 355 μm or more) of the elementary granules obtained by layering or film-coated granules obtained by film coating are removed using a sieve having a sieve opening of 355 μm, and the weight thereof is divided by the total amount and represented as % by mass.
Dissolution Test of Drug>
Since the film dissolution properties do not depend on the pH, the pH of dissolution medium is not limited but the test was carried out in accordance with "Dissolution Test" in General Tests, which clearly describes the test method, "Apparatus 2" (paddle method) is used as the apparatus with a rotation speed of paddle at 100 rpm, and the "1st fluid for dissolution test" described in the Japanese Pharmacopoeia is used as a dissolution medium.

In the case of caffeine (molecular weight 212.21), the threshold value at which the bitterness is tasted is 148.5 mg/L. Considering all the film-coated granules of Examples have the caffeine content of 1.82%, when, hypothetically speaking, 1000 mg of the film-coated granules is taken with 20 ml of water, the concentration would be 910 mg/L with the whole amount of caffeine being released. With respect to the caffeine concentration of 910 mg/L, the calculated dissolution rate of the threshold value at which the bitterness is tasted ((148.5/910)×100) is 16.3%. To assess on the stricter side, in the dissolution test, the caffeine dissolution rate of 10% or less was considered as assuring the bitterless taste in the buccal cavity. Thus, in the dissolution test, when the dissolution rate is 10% or less after 1 minute, the bitter taste was considered as suppressing bitterness. Further, as the dissolution rate after 30 minutes in the dissolution test, dissolution rate after 30 minutes of 90% or more was made requisite by using the index for the quick-release properties after dosing. Furthermore, since the film-coated granule content in a tablet varies in Examples, the dissolution test was carried out by adjusting the number of tablets so that the film-coated granule content is close to 1000 mg. (For example, when content of the film-coated granule in a tablet having the total weight of 180 mg is 30%, the dissolution test was carried out using 18 tablets in a single test solution.)

<Average Particle Size [μm] of Granulated Granule>

The particle size distribution was measured with RoTap sieve shaker (Sieve Shaker Type A, manufactured by Hirako Seisaku-sho Co., Ltd.) by screening 20 g of a sample using a JIS standard sieve for 15 minutes. The particle size of 50% by mass cumulated in the cumulative distribution under sieve was defined as an average particle size.

<Disintegration Test of Tablet>

The disintegration test was carried out in accordance with General Tests, "Disintegration Test" in the Japanese Pharmacopoeia, Fifteenth Edition. Water was used as the dissolution medium.

<Tablet Disintegration Test in Buccal Cavity>

Using three healthy adult males as the subjects, the time required for the tablet to be completely disintegrated by saliva in the buccal cavity was measured. Each subject was measured twice, and the average value of three subjects was employed.

<Abrasion Test of Tablet>

The abrasion test was carried out in accordance with General Rules for Preparations in the Japanese Pharmacopoeia, Fifteenth Edition. Twenty tablets were put in a cylindrical tube rotating at a constant rate of 25 rpm the tablets were allowed to fall repeatedly from the partition plate. After rotating for 4 minutes, the tablets were taken out from the cylindrical tube. The broken separated powders and small particles were removed by sieving, measured for the mass, and the mass reduced was shown in percentage with respect to the initial mass.

Example 1

Microcrystalline cellulose spherical core particles (GP-203 Asahi Kasei Chemicals Corporation) (having an average particle size of 237 μm, not containing particles having a particle size of 355 μm or more) were charged in a fumbling fluidized bed type coating apparatus and were sprayed and coated (layered) with an aqueous drug dispersion (3.0% caffeine, 2.0% povidone, 2.0% titanium oxide), thereby obtaining elementary granules (G1). The resulting elementary granules (G1) contained 1.95% by mass of caffeine (2% by mass based on core particle) and had an average particle size of 238 μm. The layering conditions were as below.

(1) Apparatus used: Multiplex (trade name) Type MP-25 (Powrex Corporation)
(2) Air flow: 8 $m^3$/min
(3) Charge air temperature: 70 to 75° C.
(4) Exhaust air temperature: 35.0 to 39.5° C.
(5) Rotation speed of rotor: 250 to 300 rpm
(6) Amount of core particles: 10.0 kg
(7) Amount of aqueous drug dispersion: 6660.0 kg
(8) Spray rate of aqueous drug dispersion: 100 to 120 g/min
(9) Spray air pressure: 0.55 MPa
(10) Spray air flow: 700 NL/min Subsequently, in accordance with the method described above, a film coating liquid (solid content of 17% by mass) (L1) containing an ethyl cellulose (A), an ethyl acrylate/methyl methacrylate copolymer (B), a polyvinyl alcohol copolymer (C), triethyl citrate (D) and titanium oxide (E) was prepared. Aquacoat ECD30 (FMC) as the ethyl cellulose, Eudragit NE30D (Degussa) as the ethyl acrylate/methyl methacrylate copolymer, POVACOAT (Daido Chemical Corporation) as the polyvinyl alcohol copolymer and NA61 (TOHO TITANIUM CO., LTD.) as the titanium oxide were used. The mass ratio of Components A, B, C, D and E was 100:133:33:33:33. The cast film had the tensile elongation of 250%, the tensile strength of 12.0 N, and the tackiness of "1: None".

Next, the elementary granules (G1) were charged in the tumbling fluidized bed type coating apparatus and were sprayed and coated (film-coated) with the film coating liquid (L1), and particles having a particle size of 355 μm or more were removed using a sieve, thereby obtaining film-coated granules (F1). The resulting film-coated granules (F1) had the film coating amount of 20% by mass (based on elementary granules (G1)), and the average particle size of 295.0 μm (the film thickness was about 28.5 μm). The collection ratio was 93.5%, and the agglomeration ratio was 5.7% (355 μm or more). The dissolution rates of caffeine were 5.8% after 1 minute and 96.8% after 30 minutes. The film coating conditions were as follows.

(1) Apparatus used: Multiplex (trade name) Type MP-25 (Powrex Corporation)
(2) Air flow: 73 to 8 $m^3$/min
(3) Charge air temperature: 45 to 50° C.
(4) Exhaust air temperature: 27 to 31° C.
(5) Rotation speed of rotor: 240 to 300 rpm
(6) Amount of elementary granules: 10 kg
(7) Amount of film coating liquid: 11.7 kg
(8) Spray rate of Film coating liquid: 100 to 120 g/min
(9) Spray air pressure: 0.6 MPa
(10) Spray air flow: 700 NL/min Further, in accordance with the above method, an overcoating liquid (solid content 10% by mass) (L2) containing hypromellose and water was prepared. Hydroxypropylmethyl cellulose TC-5E (Shin-Etsu Chemical Co., Ltd.) was used as the hypromellose. Next, the film-coated granules (F1) were charged in the tumbling fluidized bed type coating apparatus and were sprayed and coated (film-coated) with the overcoating liquid (L2), and particles having a particle size of 355 μm or more were removed using a sieve, thereby obtaining film-coated granules (F2) overcoated with hydroxypropylmethyl cellulose (HPMC). The resulting overcoated film-coated granules (F2) had the film coating amount of 5% by mass (based on elementary granules (G1)), and the film coating conditions for the overcoat were as follows.

(1) Apparatus used: Multiplex (trade name) Type MP-25 (Powrex Corporation)
(2) Air flow: 7.5 to 8 m³/min
(3) Charge air temperature: 60 to 70° C.
(4) Exhaust air temperature: 32 to 43° C.
(5) Rotation speed of rotor: 240 to 300 rpm
(6) Amount of elementary granules: 10.0 kg
(7) Amount of film coating liquid: 5.0 kg
(8) Spray rate of film coating liquid: 100 to 120 g/min
(9) Spray air pressure: 0.6 MPa
(10) Spray air flow: 700 NL/min Lastly, 100% by mass of the overcoated film-coated granules (F2), 163% by mass of the trehalose (Trehalose P (trade name), Hayashibara Biochemical Laboratories, Inc.), 70% by mass of the microcrystalline cellulose (Ceolus KO-802 (trade name), Asahi Kasei Chemicals Corporation), 10% by mass (outer mass percentage) of crospovidone (Polyplasdone XL-1.0, ISP), and 3.4% by mass (outer mass percentage) of the talc (TALCAN HAYASHI (trade name), (HAYASHI KASEI CO., LTD.) were mixed and subjected to tableting using a rotary tablet press (Clean Press Correct 12 HUK (trade name), Kikusui Seisakusho Ltd.). Using 12 sets of the die and punch for tableting having a diameter of 8 mm and a radius at the concave curve of the punch of 12 mm, the tableting was carried out at a turn table rotation speed of 45 rpm and a compression force of 6.6 kN, thereby obtaining a tablet of 180 mg.

The obtained tablet had the hardness of 43 N, the abrasion level of 0.13%, the disintegration time of 27 seconds, the disintegration test in the buccal cavity of 25 seconds, and the caffeine dissolution rates of 6.2% after 1 minute and of 98.9% after 30 minutes. More specifically, the quick-disintegrating tablet in the buccal cavity containing the granules coated with the film for masking the bitter taste which has a good hardness, good disintegrating properties and a drug dissolution rate of within ±10% of the dissolution rate of the film-coated granules before tableting was obtained. FIG. 1 shows the drug dissolution patterns.

Example 2

A film coating liquid (concentration of the components other than water was 37% by mass) (L3) containing Components A, B, C, D and E in the mass ratio of 100:280:33:33:33 was prepared in the same manner as in Example 1. The cast film had the tensile elongation of 350%, the tensile strength of 30 N, and the tackiness of "1: None".

Next, the same procedure as in Example 1 was carried out except that (L3) was used as the film coating liquid, thereby obtaining overcoated film-coated granules (F3). The resulting film-coated granules (F3) had the film coating amount of 20% by mass (based on elementary granules (G1)), and the average particle size of 305 μm (the film thickness was about 33.5 μm). The collection ratio was 92.0%, and the agglomeration ratio was 6.9% (355 μm or more). The dissolution rates of caffeine were 4.3% after 1 minute and 94.3% after 30 minutes.

Figure 2:
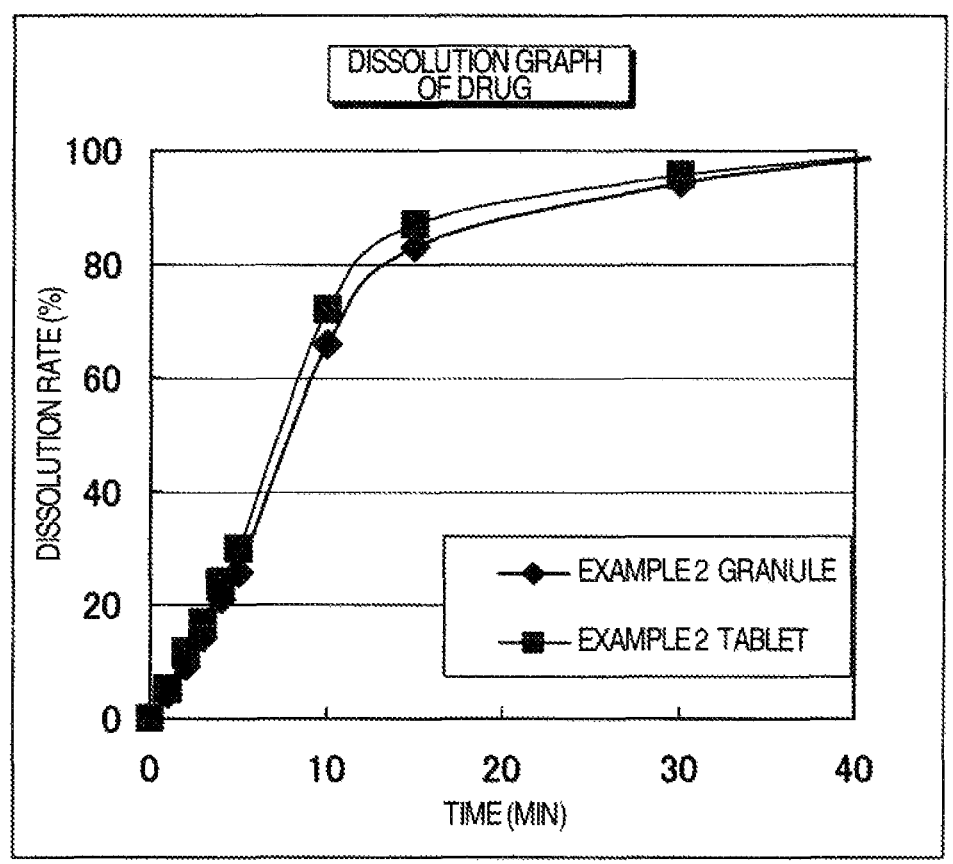
FIG. 2 is the in vitro drug dissolution profiles of the film-coated granules and the tablet containing the film-coated granules of Example 2.

Lastly, the same procedure as in Example 1 was carried out except that (F3) was used as the overcoated film-coated granules, thereby obtaining a tablet of 180 mg containing 30% by mass of the film-coated granules. The Obtained tablet had the hardness of 50 N, the abrasion level of 0.16%, the disintegration time of 28 seconds, the disintegration test in the buccal cavity of 25 seconds, and the caffeine dissolution rates of 4.6% after 1 minute and of 95.6% after 30 minutes. More specifically, the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting was obtained. FIG. 2 shows the drug dissolution patterns.

Example 3

A film coating liquid (concentration of the components other than water was 17% by mass) (L4) containing Components A, B, C, D and E in the mass ratio of 100:133:85:33:33 was prepared in the same manner as in Example 1. The cast film had the tensile elongation of 185%, the tensile strength of 11 N, and the tackiness of "1: None".

Next, the same procedure as in Example 1 was carried out except that (L4) was used as the film coating liquid, thereby obtaining overcoated film-coated granules (F4). The resulting film-coated granules (F4) had the film coating amount of 20% by mass (based on elementary granules (G1)), and the average particle size of 301 μm (the film thickness was about 31.5 μm). The collection ratio was 92.7%, and the agglomeration ratio was 5.5% (355 μm or more). The dissolution rates of caffeine were 8.5% after 1 minute and 100.0% after 30 minutes.

Figure 3:
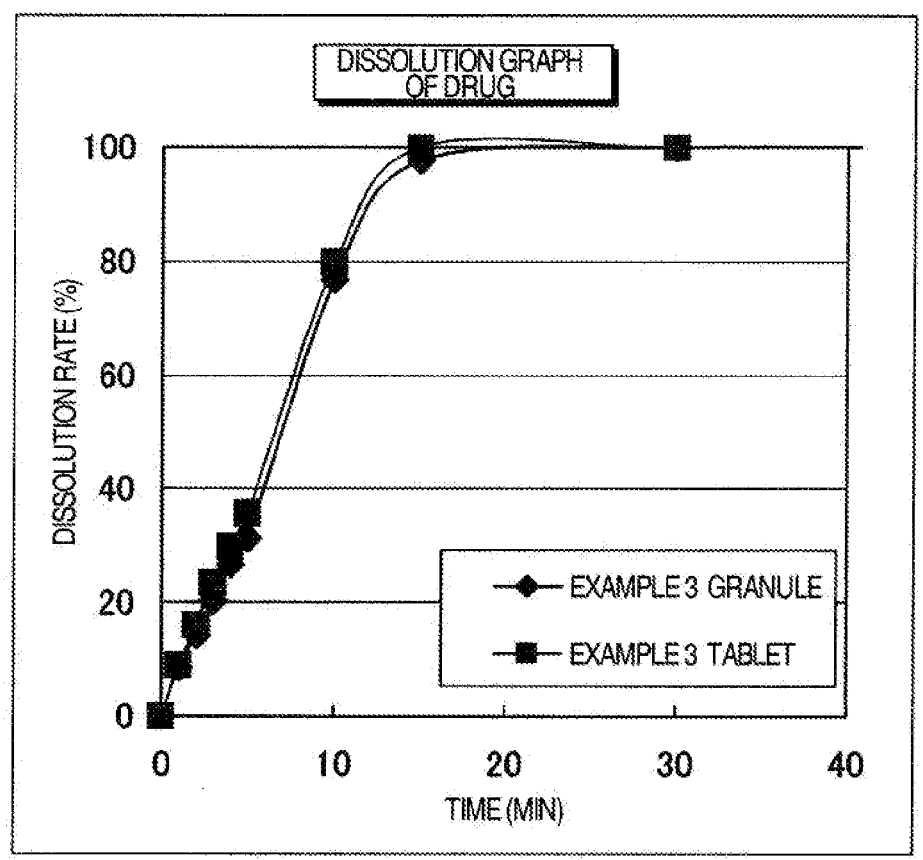
FIG. 3 is the in vitro drug dissolution profiles of the film-coated granules and the tablet containing the film-coated granules of Example 3.

Lastly, using (F4) as the overcoated film-coated granules, the same procedure as in Example 1 was carried out except that during tableting was carried out under a compression force of 5.7 kN, thereby obtaining a tablet of 180 mg containing 30% by mass of the film-coated granules. The obtained tablet had the hardness of 47 N, the abrasion level of 0.18%, the disintegration time of 25 seconds, the disintegration test in the buccal cavity of 26 seconds, and the caffeine dissolution rates of 9.0% after 1 minute and of 100.0% after 30 minutes. More specifically, the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting. FIG. 3 shows the drug dissolution patterns.

Example 4

A film coating liquid (concentration of the components other than water was 17% by mass) (L5) containing Components A, B, C, D and E in the mass ratio of 100:133:33:75:33 was prepared in the same manner as in Example 1. The cast film had the tensile elongation of 340%, the tensile strength of 24 N, and the tackiness of "1: None".

Next, the same procedure as in Example 1 was carried out except that (L5) was used as the film coating liquid, thereby obtaining overcoated film-coated granules (F5). The resulting film-coated granules (F5) had the film coating amount of 20% by mass (based on elementary granules (G1)), and the average particle size of 296 μm (the film thickness was about 29.0 μm). The collection ratio was 91.3%, and the agglomeration ratio was 6.6% (355 μm or more). The dissolution rates of caffeine were 4.2% after 1 minute and 93.1% after 30 minutes.

Figure 4:
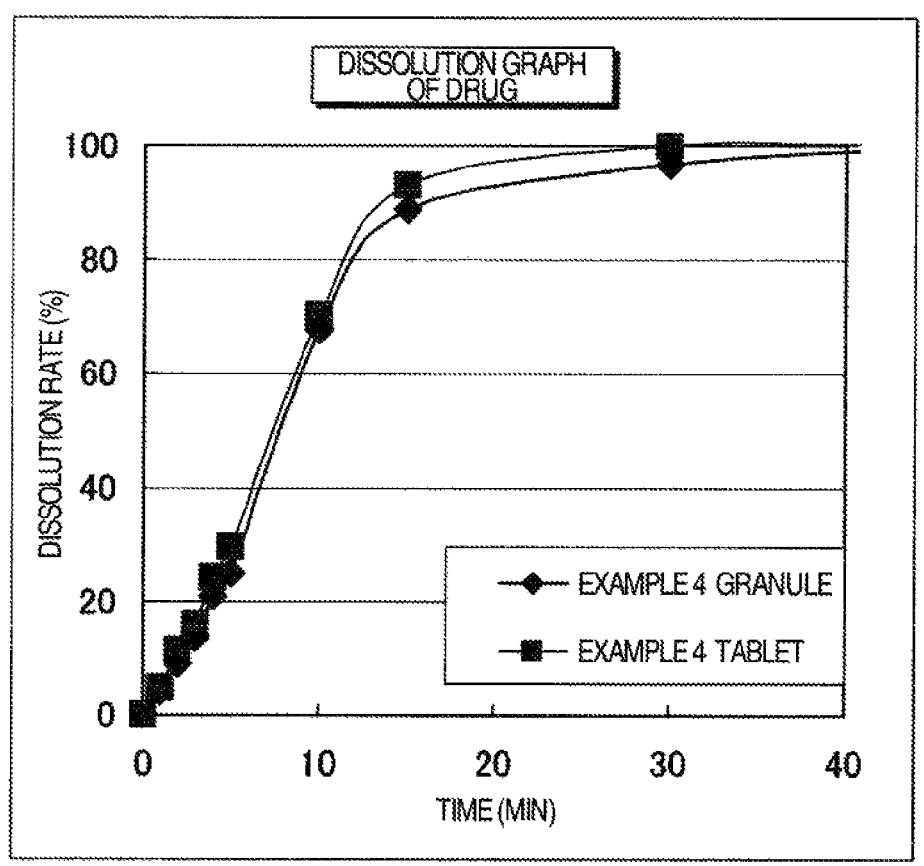
FIG. 4 is the in vitro drug dissolution profiles of the film-coated granules and the tablet containing the film-coated granules of Example 4.

Lastly, using (F5) as the overcoated film-coated granules, the same procedure as in Example 1 was carried out except that during tableting was carried out under a compression force of 8.2 kN, thereby obtaining a tablet of 180 mg containing 30% by mass of the film-coated granules. The obtained tablet had the hardness of 53 N, the abrasion level of 0.15%, the disintegration time of 28 seconds, the disintegration test in the buccal cavity of 30 seconds, and the caffeine dissolution rates of 4.6% after 1 minute and of 94.2% after 30 minutes. More specifically, the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting was obtained. FIG. 4 shows the drug dissolution patterns.

Example 5

A film coating liquid (concentration of the components other than water was 17% by mass) (L6) containing Components A, B, C, D and E in the mass ratio of 100:133:33:33:80 was prepared in the same manner as in Example 1. The cast film had the tensile elongation of 180%, the tensile strength of 10 N and the tackiness of "1: None".

Next the same procedure as in Example 1 was carried out except that (L6) was used as the film coating liquid, thereby obtaining overcoated film-coated granules (F6). The resulting film-coated granules (F6) had the film coating amount of 20% by mass (based on elementary granules (G1)), and the average particle size of 295 μm (the film thickness was about 28.5 μm). The collection ratio was 98.9%, and the agglomeration ratio was 2.0% (355 μm or more). The dissolution rates of caffeine were 7.3% after 1 minute and 100.0% after 30 minutes.

Figure 5:
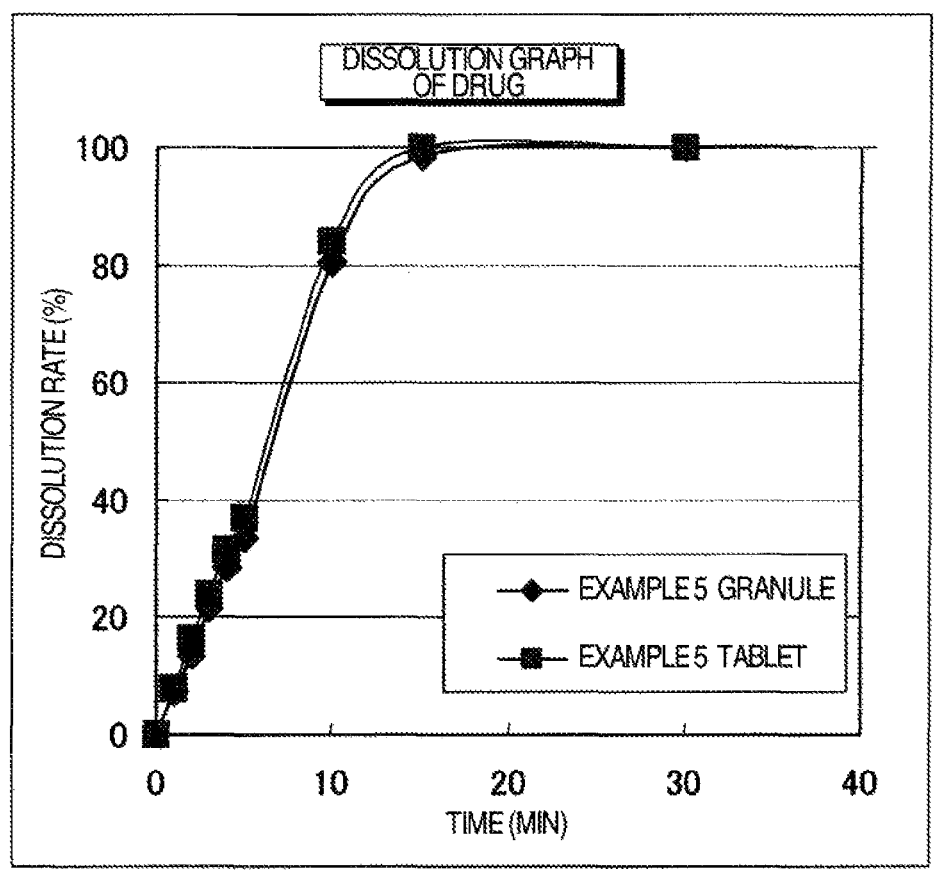
FIG. 5 is the in vitro drug dissolution profiles of the film-coated granules and the tablet containing the film-coated granules of Example 5.

Lastly, using (F6) as the overcoated film-coated granules, the same procedure as in Example 1 was carried out except that during tableting was carried out under a compression force of 7.6 kN, thereby obtaining a tablet of 180 mg containing 30% by mass of the film-coated granules. The obtained tablet had the hardness of 46 N, the abrasion level of 0.17%, the disintegration time of 26 seconds, the disintegration test; in the buccal cavity of 28 seconds, and the caffeine dissolution rates of 7.8% after 1 minute and of 100.0% after 30 minutes. More specifically, the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting was obtained. FIG. 5 shows the drug dissolution patterns.

Example 6

A film coating liquid (concentration of the components other than water was 17% by mass) (L7) containing Components A, B, C, D and E in the mass ratio of 100:350:33:33:33 was prepared in the same manner as in Example 1. The cast film had the tensile elongation of 500%, the tensile strength of 25 N, and the tackiness of "4: Strong".

Next, the same procedure as in Example 1 was carried out except that (L7) was used as the film coating liquid, thereby obtaining overcoated film-coated granules (F7). The resulting film-coated granules (F7) had the film coating amount of 20% by mass (based on elementary granules (G1)), and the average particle size of 318 μm (the film thickness was about 40.0 μm). The collection ratio was 86.8%, and the agglomeration ratio was 23.6% (355 μm or more). The dissolution rates of caffeine were 12.3% after 1 minute and 100.0% after 30 minutes.

Figure 6:
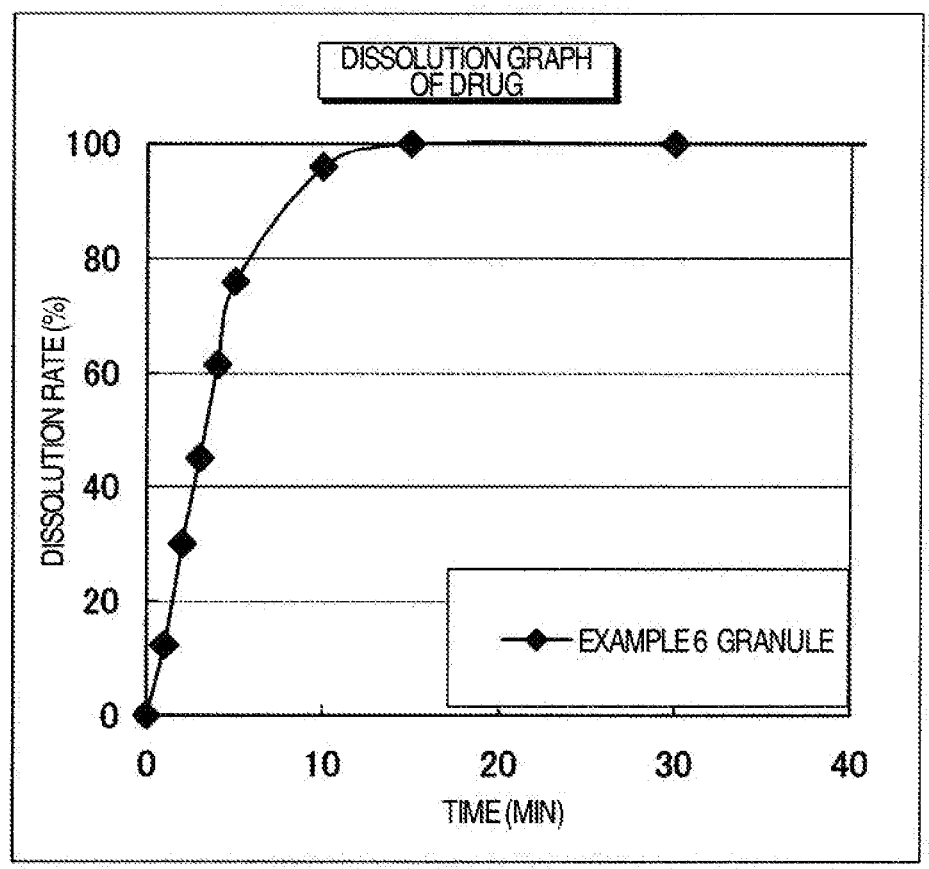
FIG. 6 is the in vitro drug dissolution profile of the film-coated granules of Example 6.

FIG. 6 shows the drug dissolution pattern.

Example 7

A film coating liquid (concentration of the components other than water was 17% by mass) (L8) containing Components A, B, C, D and E in the mass ratio of 100:133:33:95:33 was prepared in the same manner as in Example 1. The cast film had the tensile elongation of 310%, the tensile strength of 21 N, and the tackiness of "4: Strong".

Next, the same procedure as in Example 3 was carried out except that (L8) was used as the film coating liquid, thereby obtaining overcoated film-coated granules (F8). The resulting film-coated granules (F8) had the film coating amount of 20% by mass (based on elementary granules (G1)), and the average particle size of 314 μm (the film thickness was about 38 μm). The collection ratio was 83.5%, and the agglomeration ratio was 28.5% (355 μm or more). The dissolution rates of caffeine was 13.5% after 1 minute and 100.0% after 30 minutes.

Figure 7:
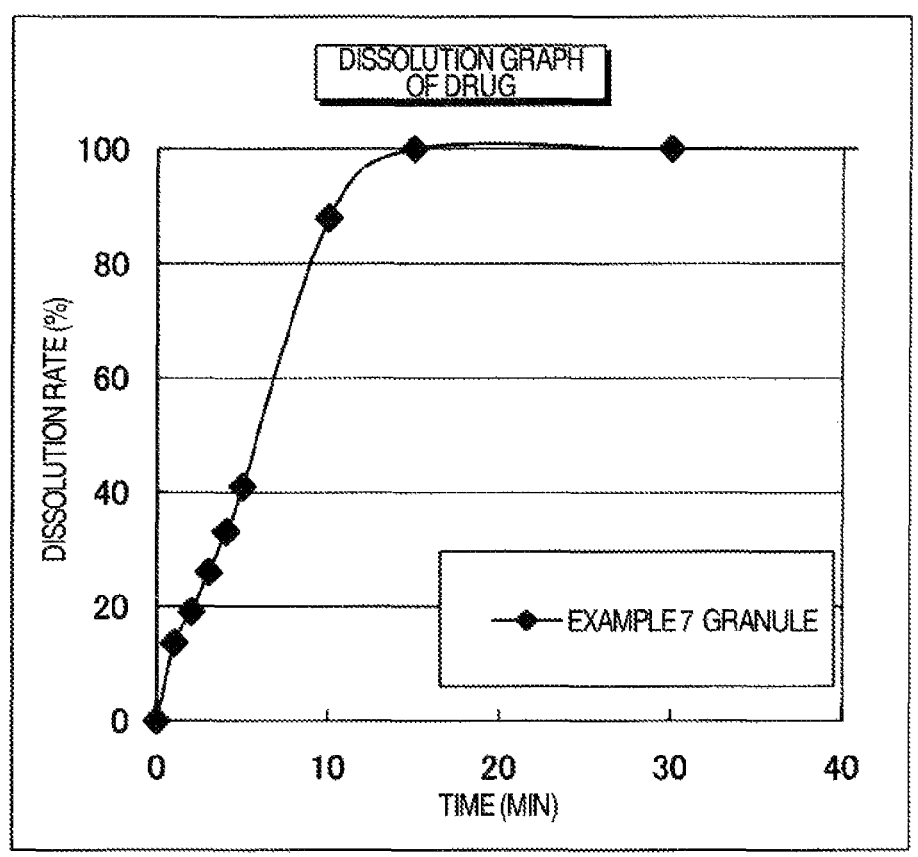
FIG. 7 is the in vitro drug dissolution profile of the film-coated granules of Example 7.

FIG. 7 shows the drug dissolution pattern.

Example 8

A film coating liquid (concentration of the components other than water was 17% by mass) (L9) containing Components A, B, C, D and E in the mass ratio of 100:133:33:33:20 was prepared in the same manner as in Example 1. The cast film had the tensile elongation of 276%, the tensile strength of 13 N, and the tackiness of "3: Weak".

Next, the same procedure as in Example 1 was carried out except that (L9) was used as the film coating liquid, thereby obtaining overcoated film-coated granules (F9). The resulting film-coated granules (F9) had the film coating amount of 20% by mass (based on elementary granules (G1)), and the average particle size of 286 μm (the film thickness was about 24 μm). The collection ratio was 94.7%, and the agglomeration ratio was 21.3% (355 μm or more). The dissolution rates of caffeine were 11.8% after 1 minute and 100.0% after 30 minutes.

Figure 8:
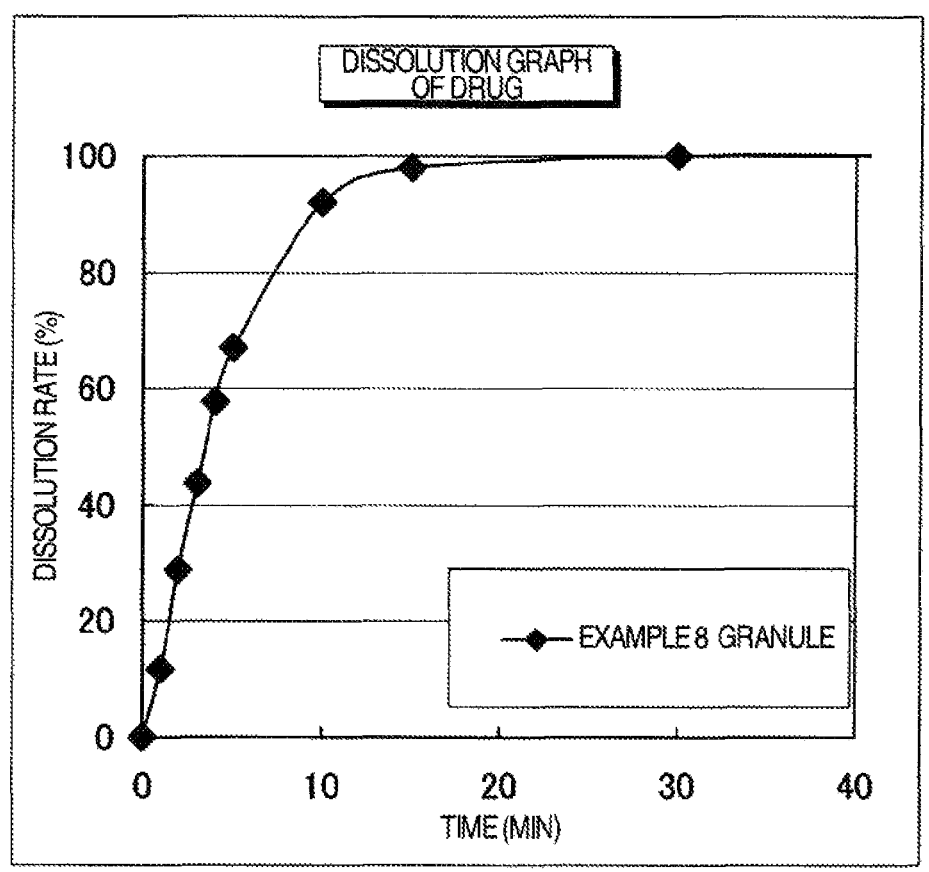
FIG. 8 is the in vitro drug dissolution profile of the film-coated granules of Example 8.

FIG. 8 shows the drug dissolution pattern.

Example 9

A film coating liquid (concentration of the components other than water was 17% by mass) (L10) containing Components A, B, C, D and E in the mass ratio of 100:133:33:33:33 was prepared in the same manner as in Example 1, except that hydroxypropylcellulose (HPC) was used as Component C. The cast film had the tensile elongation of 235%, the tensile strength of 11 N, and the tackiness of "2: Minor". Next, the same procedure as in Example 1 was carried out except that (L10) was used as the film coating liquid, thereby obtaining overcoated film-coated granules (F10). The resulting film-coated granules (F10) had the film coating amount of 20% by mass (based on elementary granules (G1)), and the average particle size of 286 μm (the film thickness was about 24 μm). The collection ratio was 94.4%, and the agglomeration ratio was 7.7% (355 μm or more). The dissolution rates of caffeine were 7.2% after 1 minute and 98.3% after 30 minutes.

Figure 9:
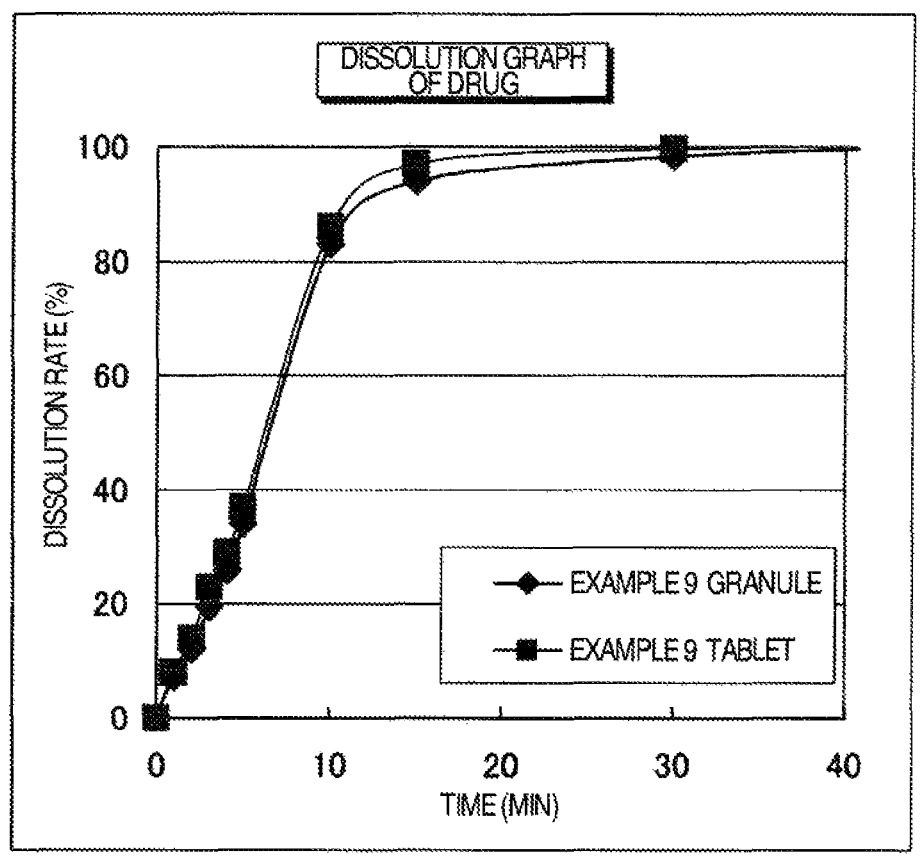
FIG. 9 is the in vitro drug dissolution profiles of the film-coated granules and the tablet containing the film-coated granules of Example 9.

Lastly, using (F10) as the overcoated film-coated granules, the same procedure as in Example 1 was carried out except that during tableting was carried out under a compression force of 6.8 kN, thereby obtaining a tablet containing 30% by mass of the film-coated granules. The obtained tablet had the hardness of 44 N, the abrasion level of 0.15%, the disintegration time of 26 seconds, the disintegration test in the buccal cavity of 27 seconds, and the caffeine dissolution rates of 7.8% after 1 minute and of 99.6% after 30 minutes. More specifically, the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting was obtained. FIG. 9 shows the drug dissolution patterns.

Example 10

A film coating liquid (concentration of the components other than water was 17% by mass) (L11) containing Components A, B, C D and E in the mass ratio of 200:133:33:33:33 was prepared in the same manner as in Example 1, except that triacetin was used as Component D. The cast film had the tensile elongation of 160%, the tensile strength of 9 N, and the tackiness of "1: None". Next, the same procedure as in Example 1 was carried out except that (L11) was used as the film coating liquid, thereby obtaining overcoated film-coated granules (F11). The resulting film-coated granules (F11) had the film coating amount of 20% by mass (based on elementary granules (G1)), and the average particle size of 280 μm (the film thickness was about 21 μm). The collection ratio was 95.7%, and the agglomeration ratio was 4.5% (355 μm or more). The dissolution rates of caffeine were 8.2% after 1 minute and 99.2% after 30 minutes.

Figure 10:
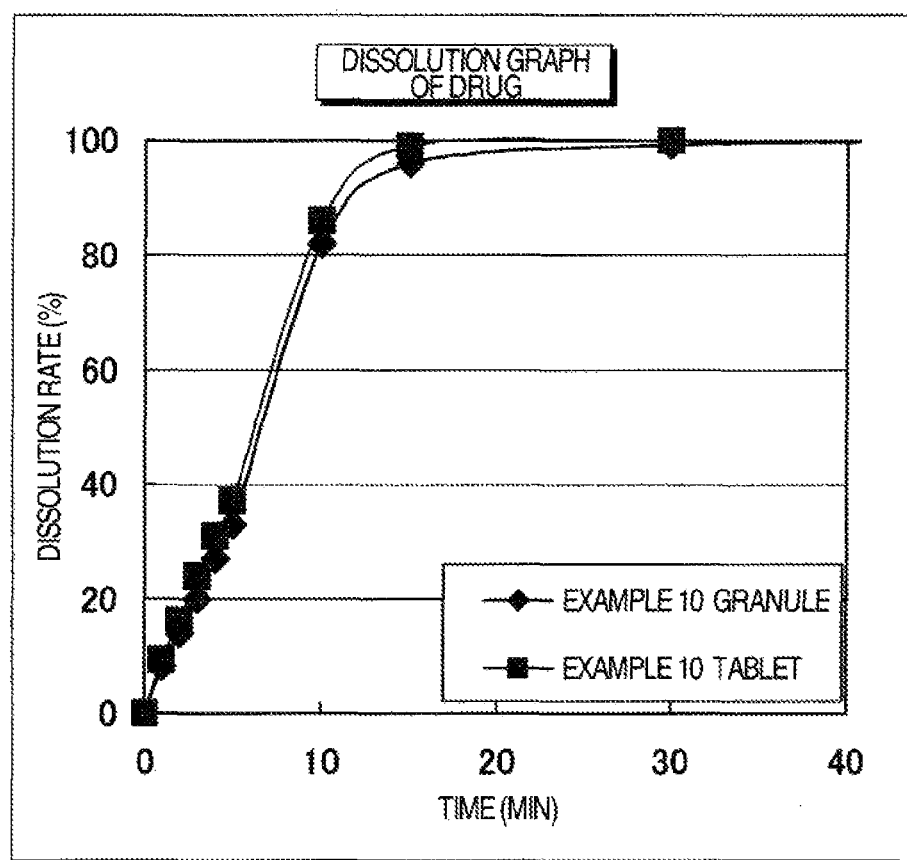
FIG. 10 is the in vitro drug dissolution profiles of the film-coated granules and the tablet containing the film-coated granules of Example 10.

Lastly, using (F11) as the overcoated film-coated granules, the same procedure as in Example 1 was carried out except that during tableting was carried out under a compression force of 8.6 kN, thereby obtaining a tablet containing 30% by mass of the film-coated granules. The obtained tablet had the hardness of 42% the abrasion level of 0.19%, the disintegration time of 28 seconds, the disintegration test in the buccal cavity of 29 seconds, and the caffeine dissolution rates of 8.9% after 1 minute and of 100.0% after 30 minutes. More specifically, the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting was obtained. FIG. 10 shows the drug dissolution patterns.

Example 11

Lastly, using the film-coated granules (F2) of Example 1, the same procedure as in Example 1 was carried out except that during tableting was carried out under a compression force of 23 kN, thereby obtaining a tablet of 180 mg.

The obtained tablet had the hardness of 105 N, the abrasion level of 0.04%, the disintegration time of 35 seconds, the disintegration test in the buccal cavity of 40 seconds, and the caffeine dissolution rates of 6.2% after 1 minute and of 99.4% after 30 minutes.

Figure 11:
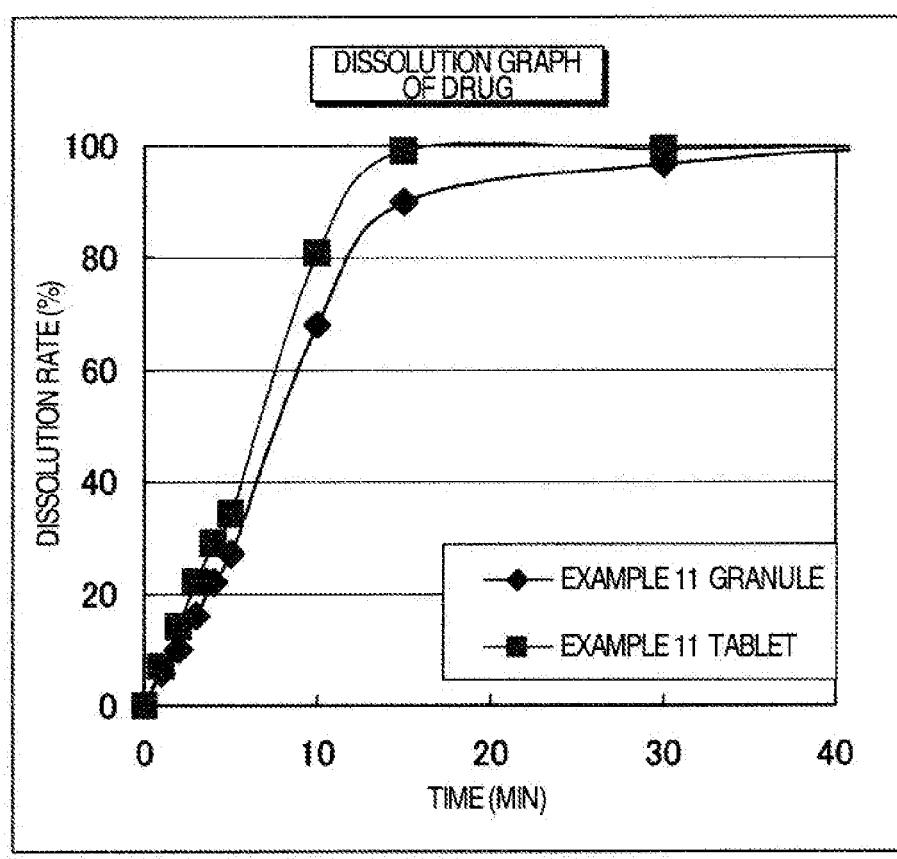
FIG. 11 is the in vitro drug dissolution profiles of the film-coated granules and the tablet containing the film-coated granules of Example 11.

More specifically, the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting was obtained. FIG. 11 shows the drug dissolution patterns.

Example 12

A film coating liquid (concentration of the components other than water was 17% by mass) (L12) containing Components A, B, C, D and E in the mass ratio of 100:133:33:33:33 was prepared in the same manner as in Example 1, except that a plasticized vinyl acetate polymer was used as Component B. The cast film had the tensile elongation of 240%, the tensile strength of 11 N, and the tackiness of "1: None".

Figure 12:
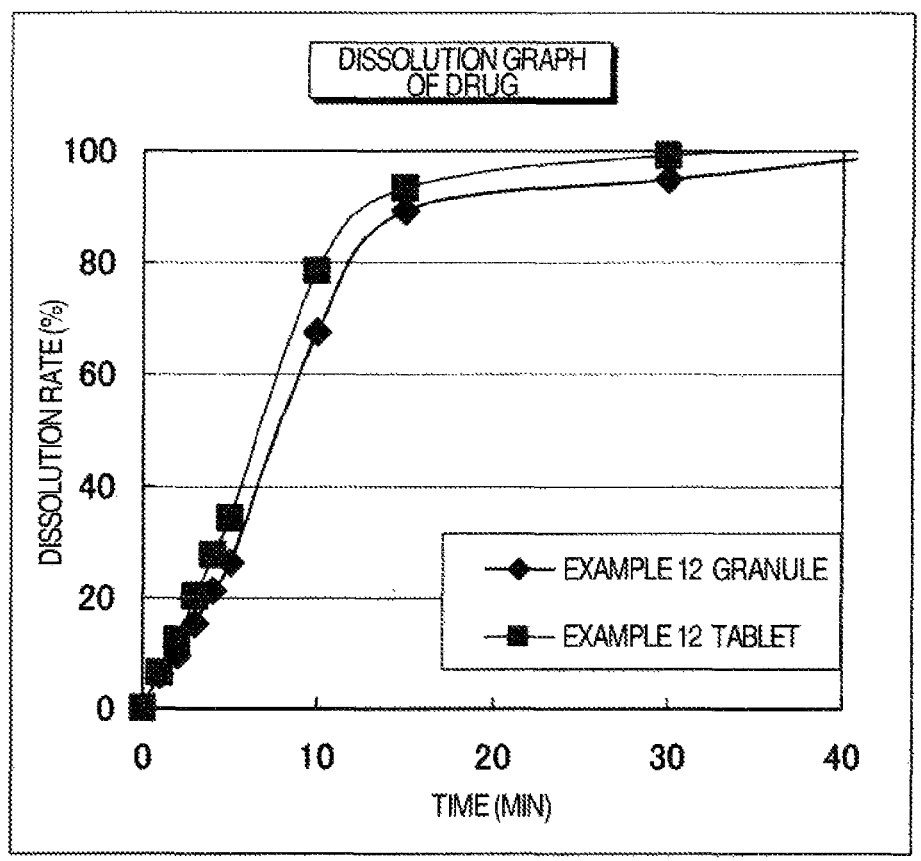
FIG. 12 is the in vitro drug dissolution profiles of the film-coated granules and the tablet containing the film-coated granules of Example 12

Next, the same procedure as in Example 1 was carried out except that (L12) was used as the film coating liquid, thereby obtaining overcoated film-coated granules (F12). The resulting film-coated granules (F12) had the film coating amount of 20% by mass (based on elementary granules (G1)), and the average particle size of 290 μm (the film thickness was about 26 μm). The collection ratio was 92.7%, and the agglomeration ratio was 5.8% (355 μm or more). The dissolution rates of caffeine were 6.0% after 1 minute and 94.9% after 30 minutes. Lastly, using (F12) as the overcoated film-coated granules, the same procedure as in Example 1 was carried out except that during tableting was earned out under a compression force of 6.6 kN, thereby obtaining a tablet containing 30% by mass of the film-coated granules. The obtained tablet had the hardness of 42 N, the abrasion level of 0.14%, the disintegration time of 28 seconds, the disintegration test in the buccal cavity of 27 seconds, and the caffeine dissolution rates of 6.5% after 1 minute and of 99.2% after 30 minutes. More specifically, the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting was obtained. FIG. 12 shows the drug dissolution patterns.

Example 13

A film coating liquid (concentration of the components other than water was 17% by mass) (L13) containing Components A, B, C, D and E in the mass ratio of 100:133:33:33:33 was prepared in the same manner as in Example 1, except that a methyl methacrylate/butyl methacrylate/dimethylaminoethyl methacrylate copolymer was used as Component C. The cast film had the tensile elongation of 245%, the tensile strength of 12 N, and the tackiness of "1: None".

Figure 13:
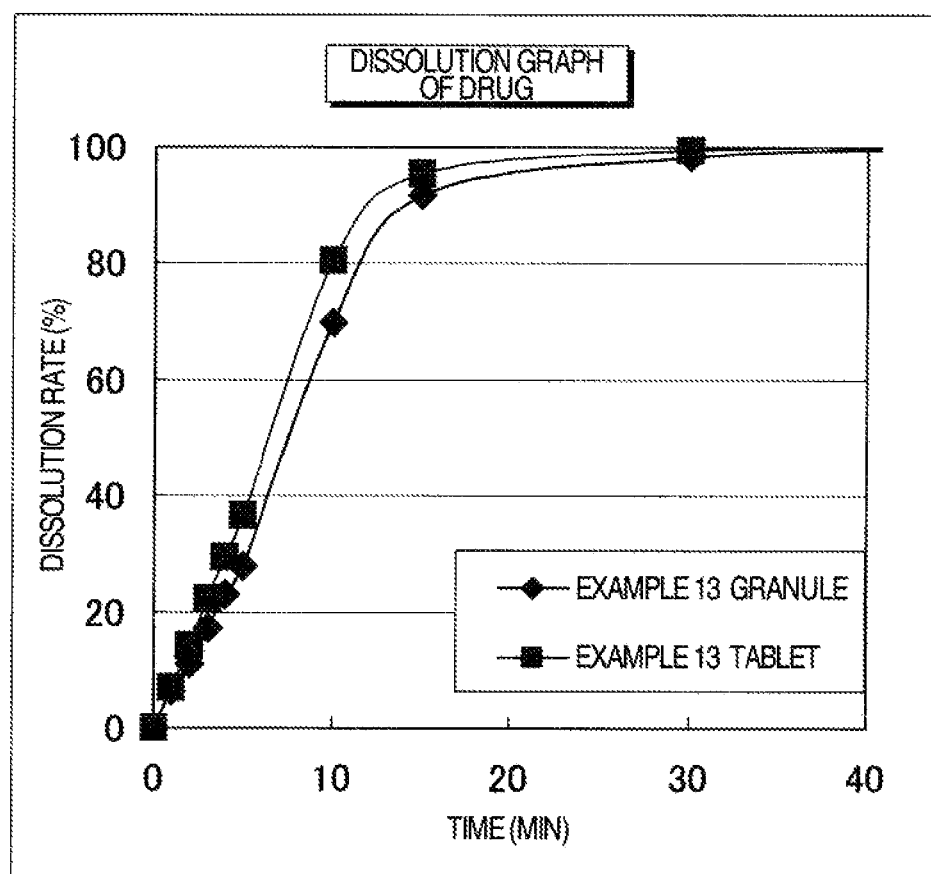
FIG. 13 is the in vitro drug dissolution profiles of the film-coated granules and the tablet containing the film-coated granules of Example 13.

Next, the same procedure as in Example 1 was carried out except that (L13) was used as the film coating liquid, thereby obtaining overcoated film-coated granules (F13). The resulting film-coated granules (F13) had the film coating amount of 20% by mass (based on elementary granules (G1)), and the average particle size of 292 μm (the film thickness was about 27 μm). The collection ratio was 94.2%, and the agglomeration ratio was 6.3% (355 μm or more). The dissolution rates of caffeine were 6.4% after 1 minute and 98.2% after 30 minutes. Lastly, using (F13) as the overcoated film-coated granules, the same procedure as in Example 1 was carried out except that during tableting was carried out under a compression force of 6.6 kN, thereby obtaining a tablet containing 30% by mass of the film-coated granules. The obtained tablet had the hardness of 43 N, the abrasion level of 0.13%, the disintegration time of 27 seconds, the disintegration test in the buccal cavity of 25 seconds, and the caffeine dissolution rates of 6.9% after 1 minute and of 99.4% after 30 minutes. More specifically the quick-disintegrating tablet in the buccal cavity containing the granules coated with the film for masking the bitter taste which has a good hardness, good disintegrating properties and the drug dissolution rate of within ±10% with respect to the dissolution rate of the film-coated granules before tableting was obtained. FIG. 13 shows the drug dissolution patterns.

Comparative Example 1

A film coating liquid (concentration of the components other than water was 17% by mass) (L14) containing Components A, B, C, D and E in the mass ratio of 100:90:33:33:33 was prepared in the same manner as in Example 1. The cast film had the tensile elongation of 130%, the tensile strength of 7 N, and the tackiness of "1: None".

Next, the same procedure as in Example 1 was carried out except that (L14) was used as the film coating liquid, thereby obtaining overcoated film-coated granules (F14). The resulting film-coated granules (F14) had the film coating amount of 20% by mass (based on elementary granules (G1)), and the average particle size of 290 μm (the film thickness was about 26.0 μm). The collection ratio was 98.6%, and the agglomeration ratio was 2.5% (355 μm or more). The dissolution rates of caffeine were 6.3% after 1 minute and 97.8% after 30 minutes.

Lastly, using (F14) as the overcoated film-coated granules, the same procedure as in Example 1 was carried out except that during tableting was carried under a compression force of 7.5 kN, thereby obtaining a tablet containing 30% by mass of the film-coated granules. The obtained tablet had the hardness of 45 N, the abrasion level of 0.15%, the disintegration time of 25 seconds, the disintegration test in the buccal cavity of 27 seconds, and the caffeine dissolution rates of 13.7% after 1 minute and of 100.0% after 30 minutes.

Figure 14:
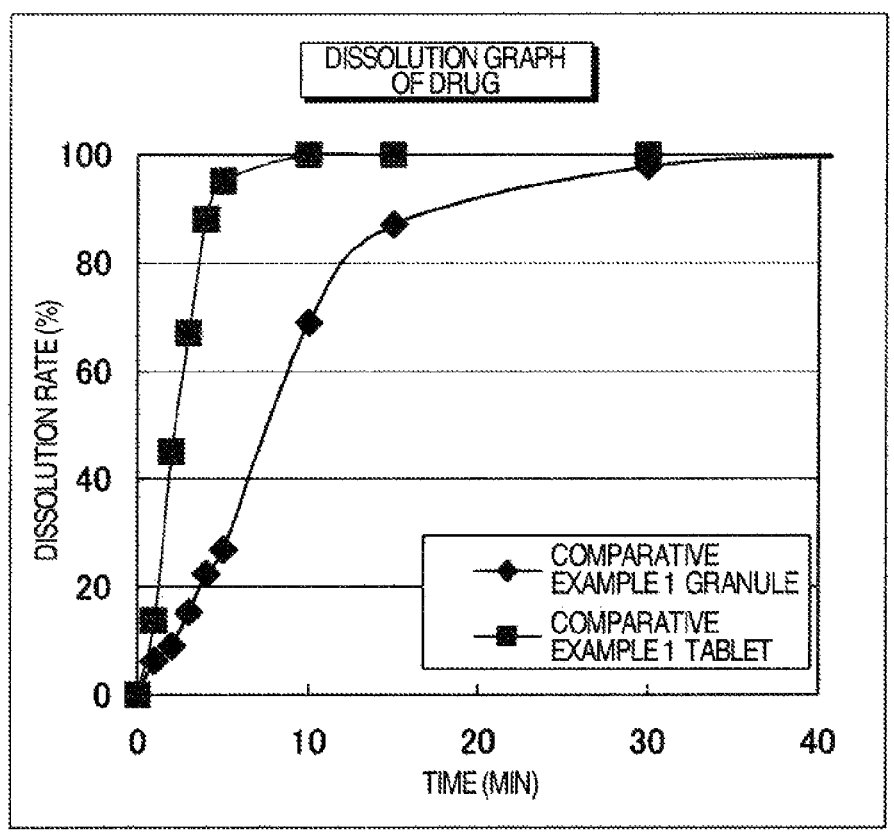
FIG. 14 is the in vitro drug dissolution profiles of the film-coated granules and the tablet containing the film-coated granules of Comparative Example 1.

That is, the insufficient mixing ratio of the ethyl acrylate/methyl methacrylate copolymer (B) caused the lack of elongation and strength of the film due to which the film was damaged by the compression force during tableting, hence resulting in the sped-up drug dissolution. FIG. 14 shows the drug dissolution patterns.

Comparative Example 2

A film coating liquid (concentration of the components other than water was 17% by mass) (L15) containing Components A, B, C, D and E in the mass ratio of 100:133:95:33:33 was prepared in the same manner as in Example 1. The cast film had the tensile elongation of 120%, the tensile strength of 6 N, and the tackiness of "3: None".

Next, the same procedure as in Example 1 was carried out except that (L15) was used as the film coating liquid, thereby obtaining overcoated film-coated granules (F15). The resulting film-coated granules (F15) had the film coating amount of 20% by mass (based on elementary granules (G1)), and the average particle size of 302 μm (the film thickness was about 32 μm). The collection ratio was 98.3%, and the agglomeration ratio was 2.8% (355 μm or more). The dissolution rates of caffeine were 14.5% after 1 minute and 100.0% after 30 minutes.

Figure 15:
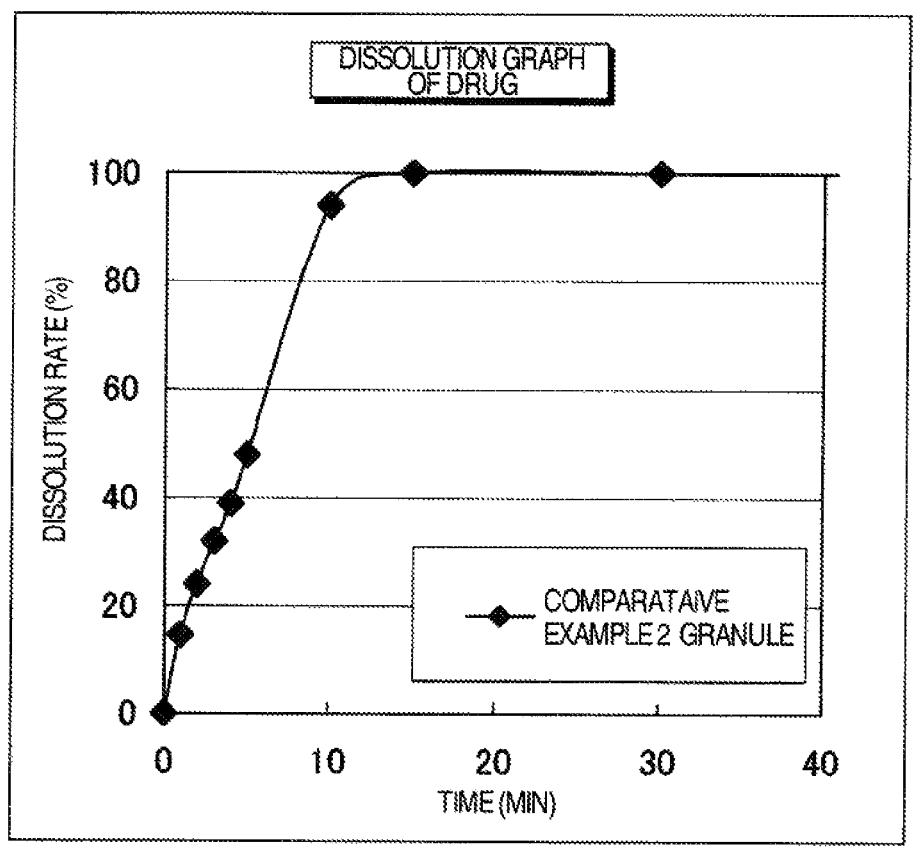
FIG. 15 is the in vitro drug dissolution profile of the film-coated granules of Comparative Example 2.

That is, the excessive mixing ratio of the polyvinyl alcohol copolymer (C) reduced the elongation and strength of the film, and also being a water-soluble component facilitated the drug dissolution rate, thus failing to provide a dissolution rate of 10% or less in 1 minute. FIG. 15 shows the drug dissolution pattern.

Comparative Example 3

A film coating liquid (concentration of the components other than water was 17% by mass) (L16) containing Components A, B, C, D and E in the mass ratio of 100:333:33:33:95 was prepared in the same manner as in Example 1. The cast film had the tensile elongation of 110%, the tensile strength of 5 N, and the tackiness of "1: None", Next, the same procedure as in Example 1 was carried out except that (L16) was used as the film coating liquid, thereby obtaining overcoated film-coated granules (F16). The resulting film-coated granules (F16) had the film coating amount of 20% by mass (based on elementary granules (G1)), and the average particle size of 320 μm (the film thickness was about 41 μm). The collection ratio was 98.2%, and the agglomeration ratio was 3.0% (355 μm or more). The dissolution rates of caffeine were 6.2% after 1 minute and 93.0% after 30 minutes.

Lastly, the same procedure as in Example 1 was carried out except that (F16) was used as the overcoated film-coated granules, thereby obtaining a tablet containing 30% by mass of the film-coated granules. The obtained tablet had the hardness of 43 M, the abrasion level of 0.13%, the disintegration time of 27 seconds, the disintegration test in the buccal cavity of 25 seconds, and the caffeine dissolution rates of 14.5% after 1 minute and of 100.0% after 30 minutes.

Figure 16:
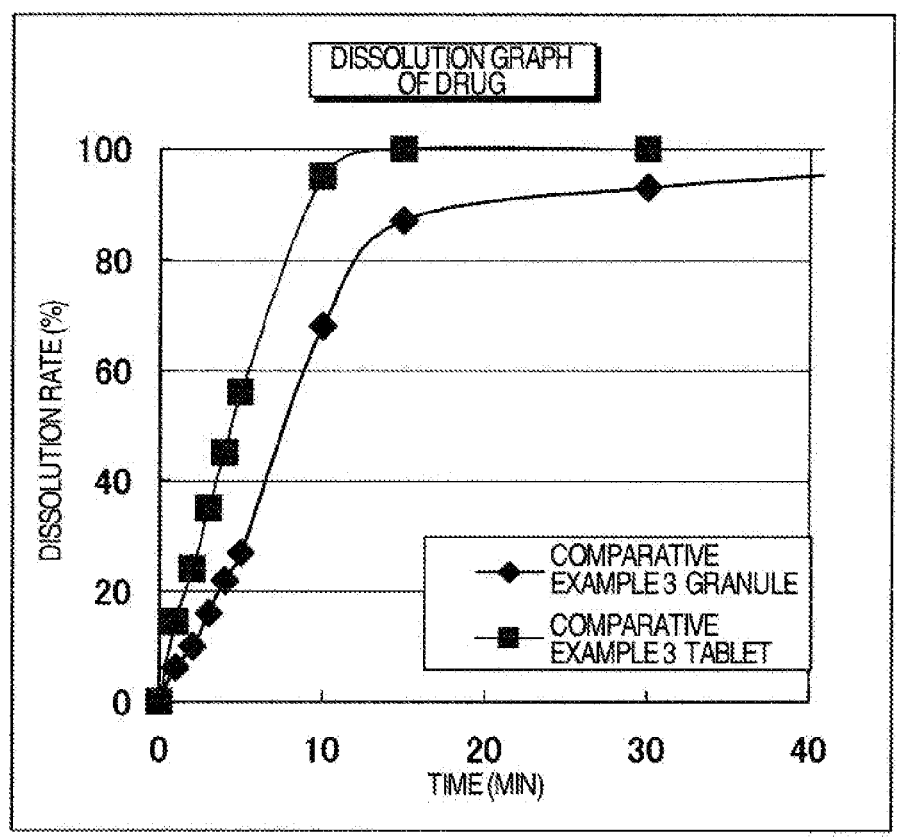
FIG. 16 is the in vitro drug dissolution profiles of the film-coated granules and the tablet containing the film-coated granules of Comparative Example 3.

That is, the excessive mixing ratio of the titanium oxide (E) reduced the elongation and strength of the film, and the film coating the film-coated granules was damaged after tableting which facilitated the drug dissolution rate, thus failing to provide a dissolution rate of 10% or less in 1 minute. FIG. 16 shows the drug dissolution patterns.

Tables 1 to 2 below show the formulation and evaluation of Examples and Comparative Examples.

TABLE 1

Table for solid mass ratios and measurement results of Examples

| | Example 1 | Example 2 | Example 3 | Example 4 |
|---|---|---|---|---|
| Step: Film coating | | | | |
| Core particle (microcrystalline cellulose core particle) | CP-203 | CP-203 | CP-203 | CP-203 |
| [A] Ethyl cellulose (solid content % by mass) | 100 | 100 | 100 | 100 |
| [B] Ethyl acrylate/methyl methacrylate copolymer dispersion (solid content % by mass) | 133 | 280 | 133 | 133 |
| [B] Plasticized vinyl acetate polymer (solid content % by mass) | | | | |
| [C] Pharmaceutical additive (solid content % by mass) | 33 | 33 | 85 | 33 |
| polyvinyl alcohol copolymer HPC | | | | |
| methyl methacrylate/butyl methacrylate/dimethylaminoethyl methacrylate copolymer | | | | |
| [D] Plasticizer (% by mass) | 33 | 33 | 33 | 75 |
| Triethyl citrate Triacetin | | | | |
| [E] Titanium oxide (solid content % by mass) | 33 | 33 | 33 | 33 |
| Film coating liquid solid content (% by mass) | 17 | 17 | 17 | 17 |
| Cast film tensile elongation (%) | 250% | 350% | 185% | 340% |
| Cast film strength (N) | 12 | 30 | 11 | 24 |
| Cast film tackiness | 1: None | 1: None | 1: None | 1: None |

TABLE 1-continued

Table for solid mass ratios and measurement results of Examples

| | | | | |
|---|---|---|---|---|
| [F] Bitterness-masked film-coated granule Average particle size (μm) | 295 μm | 305 μm | 301 μm | 296 μm |
| Collection ratio (%) | 93.5% | 92.0% | 92.7% | 91.3% |
| Agglomeration ratio (%) | 5.7% | 6.9% | 5.5% | 6.6% |
| Overcoat | HPMC | HPMC | HPMC | HPMC |
| Granule: drug dissolution rate (%) after 1 minute | 5.8% | 4.3% | 8.5% | 4.2% |
| Granule: drug dissolution rate (%) after 30 minutes | 9.68% | 94.3% | 100.0% | 93.1% |
| Step: Tableting | | | | |
| [F] bitterness-masked film-coated granules (% by mass) | 100 | 100 | 100 | 100 |
| [a] Trehalose (% by mass) | 163 | 163 | 163 | 163 |
| [b] Microcrystalline cellulose [KG-802](% by mass) | 70 | 70 | 70 | 70 |
| [c] Disintegrant (% by mass) | 10 | 10 | 10 | 10 |
| [d] Lubricant (% by mass) | 3.4 | 3.4 | 3.4 | 3.4 |
| Compression force (kN) | 6.6 | 6.6 | 5.7 | 8.2 |
| Tablet hardness (N) | 43 | 50 | 47 | 53 |
| Tablet abrasion level (%) | 0.13 | 0.16 | 0.18 | 0.15 |
| Tablet disintegration test time (sec) | 27 | 28 | 25 | 28 |
| Tablet disintegration time in buccal cavity | 25 | 25 | 26 | 30 |
| Tablet: drug dissolution rate (%) after 1 minute | 6.2% | 4.6% | 9.0% | 4.6% |
| Tablet: drug dissolution rate (%) after 30 minutes | 98.9% | 95.6% | 100.0% | 94.2% |

| | Example 5 | Example 6 | Example 7 | Example 8 | Example 9 | Example 10 | Example 11 | Example 12 | Example 13 |
|---|---|---|---|---|---|---|---|---|---|
| Step: Film coating | | | | | | | | | |
| Core particle (microcrystalline cellulose core particle) | CP-203 | CP-203 | CP-203 | CP-203 | CP-203 | CP-203 | CP-203 | CP-203 | CP-203 |
| [A] Ethyl cellulose (solid content % by mass) | 100 | 100 | 100 | 100 | 100 | 100 | 100 | 100 | 100 |
| [B] Ethyl acrylate/methyl methacrylate copolymer dispersion (solid content % by mass) | 133 | 350 | 133 | 133 | 133 | 133 | 133 | 133 | 133 |
| [B] Plasticized vinyl acetate polymer (solid content % by mass) | | | | | | | | | |
| [C] Pharmaceutical additive (solid content % by mass) polyvinyl alcohol copolymer HPC methyl methacrylate/butyl methacrylate/dimethylaminoethyl methacrylate copolymer | 33 | 33 | 33 | 33 | 33 | 33 | 33 | 33 | 33 |
| [D] Plasticizer (% by mass) Triethyl citrate Triacetin | 33 | 33 | 95 | 33 | 33 | 33 | 33 | 33 | 33 |
| [E] Titanium oxide (solid content % by mass) | 80 | 33 | 33 | 20 | 33 | 33 | 33 | 33 | 33 |
| Film coating liquid solid content (% by mass) | 17 | 17 | 17 | 17 | 17 | 17 | 17 | 17 | 17 |
| Cast film tensile elongation (%) | 180% | 500% | 310% | 276% | 235% | 160% | 250% | 240% | 245% |
| Cast film strength (N) | 10 | 25 | 21 | 13 | 11 | 9 | 12 | 11 | 12 |
| Cast film tackiness | 1: None | 4: Strong | 4: Strong | 3: Weak | 2: Minor | 1: None | 1: None | 1: None | 1: None |
| [F] Bitterness-masked film-coated granule Average particle size (μm) | 295 μm | 318 | 314 | 286 | 286 μm | 280 μm | 295 μm | 290 μm | 292 μm |
| Collection ratio (%) | 98.9% | 86.8% | 83.5% | 94.7% | 94.4% | 95.7% | 93.5% | 92.7% | 94.2% |
| Agglomeration ratio (%) | 2.0% | 23.6% | 28.5% | 21.3% | 7.7% | 4.5% | 5.7% | 5.8% | 6.3% |
| Overcoat | HPMC | HPMC | HPMC | HPMC | HPMC | HPMC | HPMC | HPMC | HPMC |
| Granule: drug dissolution rate (%) after 1 minute | 7.3% | 12.3% | 13.5% | 11.8% | 7.2% | 8.2% | 5.8% | 6.0% | 6.4% |
| Granule: drug dissolution rate (%) after 30 minutes | 100.0% | 100.0% | 100.0% | 100.0% | 98.3% | 99.2% | 96.8% | 94.9% | 98.2% |
| Step: Tableting | | | | | | | | | |
| [F] bitterness-masked film-coated granules (% by mass) | 100 | | | | 100 | 100 | 100 | 100 | 100 |
| [a] Trehalose (% by mass) | 163 | | | | 163 | 163 | 163 | 163 | 163 |
| [b] Microcrystalline cellulose [KG-802] (% by mass) | 70 | | | | 70 | 70 | 70 | 70 | 70 |
| [c] Disintegrant (% by mass) | 10 | | | | 10 | 10 | 10 | 10 | 10 |
| [d] Lubricant (% by mass) | 3.4 | | | | 3.4 | 3.4 | 3.4 | 3.4 | 3.4 |
| Compression force (kN) | 7.6 | | | | 6.8 | 8.6 | 23 | 6.6 | 6.6 |
| Tablet hardness (N) | 46 | | | | 44 | 42 | 105 | 42 | 43 |
| Tablet abrasion level (%) | 0.17 | | | | 0.15 | 0.19 | 0.04 | 0.14 | 0.13 |
| Tablet disintegration test time (sec) | 26 | | | | 26 | 28 | 35 | 28 | 27 |
| Tablet disintegration time in buccal cavity | 28 | | | | 27 | 29 | 40 | 27 | 25 |
| Tablet: drug dissolution rate (%) after 1 minute | 7.8% | | | | 7.8% | 8.9% | 6.2% | 6.5% | 6.9% |
| Tablet: drug dissolution rate (%) after 30 minutes | 100.0% | | | | 99.6% | 100.0% | 99.4% | 99.2% | 99.4% |

TABLE 2

Table for solid mass ratios and measurement results of Comparative Examples

|  | Comparative Example 1 | Comparative Example 2 | Comparative Example 3 |
|---|---|---|---|
| Step: Film coating |  |  |  |
| Core particle (microcrystalline cellulose core particle) | CP-203 | CP-203 | CP-203 |
| [A] Ethyl cellulose (solid content % by mass) | 100 | 100 | 100 |
| [B] Ethyl acrylate/methyl methacrylate copolymer dispersion (solid content % by mass) | 90 | 133 | 133 |
| [C] Polyvinyl alcohol copolymer (solid content % by mass) | 33 | 95 | 33 |
| [D] Triethyl citrate (% by mass) | 33 | 33 | 33 |
| [E] Titanium oxide (solid content % by mass) | 33 | 33 | 95 |
| Film coating liquid solid content | 17 | 17 | 17 |
| Cast film tensile elongation (%) | 130% | 120% | 110% |
| Cast film strength (N) | 7 | 6 | 5 |
| Cast film tackiness | 1: None | 1: None | 1: None |
| [F] Bitterness-masked film-coated particle Average particle size (μm) | 290 μm | 302 | 320 |
| Collection ratio (%) | 98.6% | 98.3% | 98.2% |
| Agglomeration ratio (%) | 2.5% | 2.8% | 3.0% |
| Overcoat | HPMC | HPMC | HPMC |
| Granule: drug dissolution rate (%) after 1 minute | 6.3% | 14.5% | 6.2% |
| Granule: drug dissolution rate (%) after 30 minutes | 97.8% | 100.0% | 93.0% |
| Step: Tableting |  |  |  |
| [F] Bitterness-masked film-coated granule (% by mass) | 100 |  | 100 |
| [a] Trehalose (% by mass) | 163 |  | 163 |
| [b] Microcrystalline cellulose [KG-802] (% by mass) | 70 |  | 70 |
| [c] Disintegrant (% by mass) | 10 |  | 10 |
| [d] Lubricant (% by mass) | 3.4 |  | 3.4 |
| Compression force (kN) | 7.5 |  | 6.6 |
| Tablet hardness (N) | 45 |  | 43 |
| Tablet abrasion level (%) | 0.15 |  | 0.13 |
| Tablet disintegration test time (sec) | 25 |  | 27 |
| Tablet disintegration time in buccal cavity (sec) | 27 |  | 25 |
| Tablet: drug dissolution rate (%) after 1 minute | 13.7% |  | 14.5% |
| Tablet: drug dissolution rate (%) after 30 minutes | 100.0% |  | 100.0% |

INDUSTRIAL APPLICABILITY

The present invention can be preferably used in the field of pharmaceutical preparations containing a pharmaceutical drug. The granules coated with the film of the present invention particularly has good disintegrating properties, and hence is applicable as the disintegrating solid preparations which can be taken without water, preferably as the quick-disintegrating solid preparation (tablet) in the buccal cavity.

The invention claimed is:

1. A coating film comprising
Component A: an ethyl cellulose, Component B: an ethyl acrylate/methyl methacrylate copolymer, Component C: a polyvinyl alcohol copolymer, Component D: a plasticizer, and Component E: an inorganic substance, wherein a mass ratio of the Components A:B:C:D:E is 100:(100 to 200):(6 to 90):(6 to 90):(30 to 90), and having a tensile elongation of 150% or more and a tensile strength of 9 N or more.

2. The coating film according to claim 1, wherein Component D is triethyl citrate.

3. The coating film according to claim 1, wherein Component E is titanium oxide.

4. A granule comprising a drug-containing elementary granule having the periphery thereof coated with a coating film, and having a drug dissolution rate of 10% or less in 1 minute and 90% or more in 30 minutes,
wherein "1st fluid for dissolution test" described in Japanese Pharmacopoeia is used as a dissolution medium by paddle method with a rotation speed of paddle at 100 rpm,
and further having an agglomeration ratio of 10% or less,
wherein the coating film is a coating film comprising Component A: an ethyl cellulose, Component B: an ethyl acrylate/methyl methacrylate copolymer, Component C: a polyvinyl alcohol copolymer, Component D: a plasticizer, and Component E: an inorganic substance, wherein a mass ratio of Components A:B:C:D:E is 100:(100 to 200):(6 to 90):(6 to 90):(30 to 90), and having a tensile elongation of 150% or more and a tensile strength of 9 N or more.

5. The granule according to claim 4, wherein the granule coating film has only a single layer and a drug dissolution rate when a compression force of maximum 25 kN is applied to the granule is within +/−10% of a drug dissolution rate of the granule to which a compression force is not applied.

6. The granule according to claim 5, wherein the elementary granule contains a spherical core particle containing 70% by mass or more of a microcrystalline cellulose.

7. A tablet containing 0.55 to 90.0% by mass of the granule according to claim 6.

8. The tablet according to claim 7, further containing trehalose, a microcrystalline cellulose, a disintegrant, and a lubricant.

9. The tablet according to claim 8, wherein a mass ratio of granule:trehalose:microcrystalline cellulose:disintegrant:lubricant is 100:(30 to 6900):(12 to 3000):(0.1 to 1000):(0.1 to 1000).

* * * * *